United States Patent
Michnick et al.

(12) 
(10) Patent No.: US 6,428,951 B1
(45) Date of Patent: *Aug. 6, 2002

(54) PROTEIN FRAGMENT COMPLEMENTATION ASSAYS FOR THE DETECTION OF BIOLOGICAL OR DRUG INTERACTIONS

(75) Inventors: Stephen William Watson Michnick; Joelle Nina Pelletier, both of Westmount; Ingrid Remy, Montreal, all of (CA)

(73) Assignee: Odyssey Pharmaceuticals, Inc., San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/499,464

(22) Filed: Feb. 7, 2000

Related U.S. Application Data

(63) Continuation of application No. 09/017,412, filed on Feb. 2, 1998, now Pat. No. 6,270,964.

(30) Foreign Application Priority Data

Jan. 31, 1997 (CA) ............................................ 2196496

(51) Int. Cl.[7] ............................ C12Q 1/25; C12Q 1/68; C07K 14/00; C12N 15/11
(52) U.S. Cl. .............................. 435/4; 435/6; 530/350; 536/23.2; 536/23.4
(58) Field of Search ..................... 435/4, 6; 530/350; 536/23.2, 23.4

(56) References Cited

PUBLICATIONS

Johnsson et al., Split ubiquitin as a sensor of protein interactions in vivo, Proc. Natl. Acad. Sci. USA, vol. 91, pp 10340–10344, Oct. 1994, Biochemistry.*

Pelletier et al., Oligomerization domain–directed reassembly of active dihydrofolate reductase from rationally designed fragments, Proc. Natl. Sci USA, vol. 95, pp 12141–12146, Biochemistry.*

* cited by examiner

Primary Examiner—John S. Brusca
(74) Attorney, Agent, or Firm—Isaac A. Angres; Susan P. Petraglia

(57) ABSTRACT

We describe a strategy for designing and implementing protein-fragment complementation assays (PCAs) to detect biomolecular interactions in vivo and in vitro. The design, implementation and broad applications of this strategy are illustrated with a large number of enzymes with particular detail provided for the example of murine dihydrofolate reductase (DHFR). Fusion peptides consisting of N- and C-terminal fragments of murine DHFR fused to-GCN4 leucine zipper sequences were coexpressed in *Escherichia coli* grown in minimal medium, where the endogenous DHFR activity was inhibited with trimethoprim. Coexpression of the complementary fusion products restored colony formation. Survival only occurred when both DHFR fragments were present and contained leucine-zipper forming sequences, demonstrating that reconstitution of enzyme activity requires assistance of leucine zipper formation. DHFR fragment-interface point mutants of increasing severity (Ile to Val, Ala and Gly) resulted in a sequential increase in *E. coli* doubling times illustrating the successful DHFR fragment reassembly rather than non-specific interactions between fragments. This assay could be used to study equilibrium and kinetic aspects of molecular interactions including protein-protein, protein-DNA, protein-RNA, protein-carbohydrate and protein-small molecule interactions, for screening cDNA libraries for binding of a target protein with unknown proteins or libraries of small organic molecules for biological activity. The selection and design criteria applied here is developed for numerous examples of clonal selection, colorometric, fluorometric and other assays based on enzymes whose products can be measured. The development of such assay systems is shown to be simple, and provides for a diverse set of protein fragment complementation applications.

18 Claims, 7 Drawing Sheets

FIG. 5

Creation of DHFR fragments:

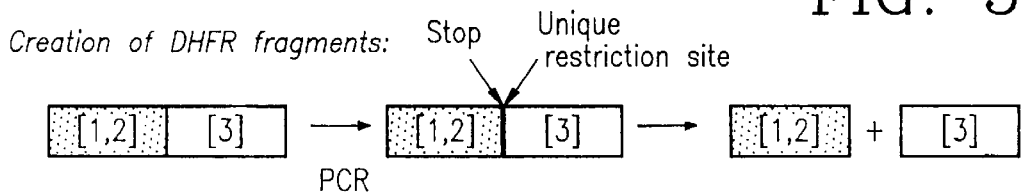

Insertion of fragments into pQE-32 for bacterial screening,
or pMT3 or Zap Express for eukaryotic screening:

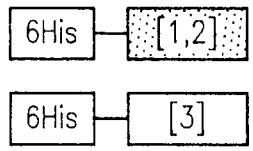

Note: For eukaryotic expression, the
expressed constructs have no
hexahistidine tag.

Insertion of targets or unknowns
(including directional insertion of cDNA library):

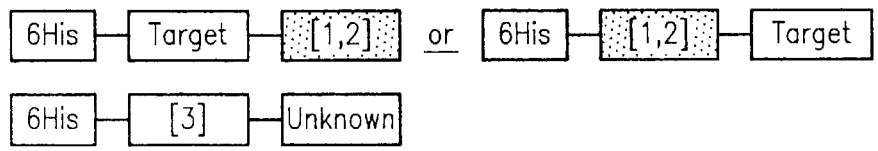

Survival assays:

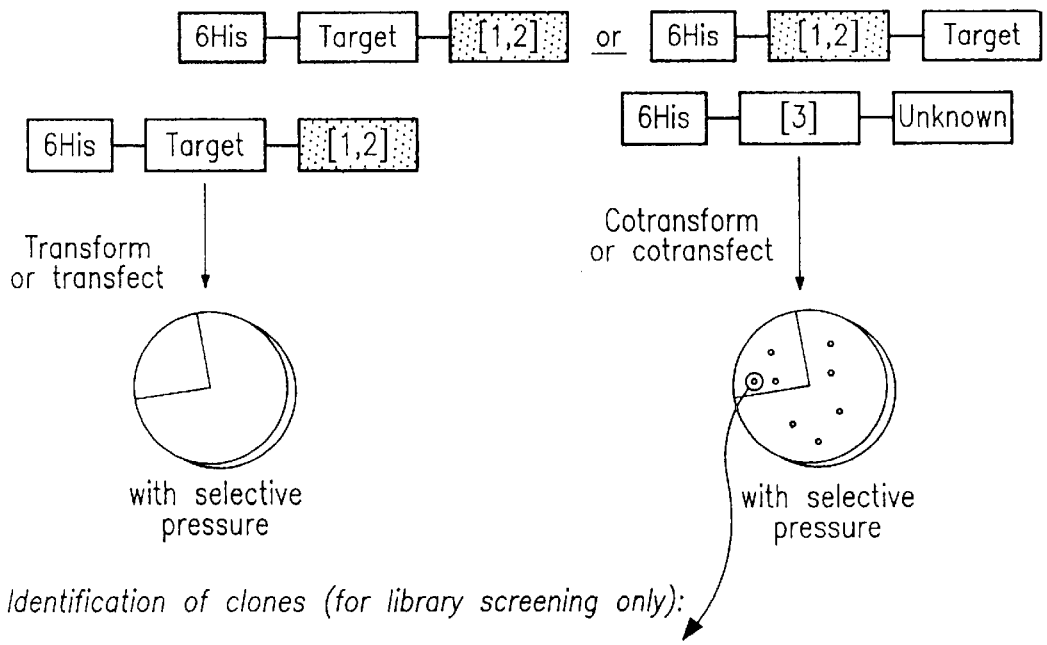

Identification of clones (for library screening only):

- Propagation of cells (bacterial or eukaryotic)
- Isolation of plasmid DNA and insert sequencing
- For bacterial screening only: overexpression and one-step purification of fusion products by the hexahistidine tag

FIG. 7
Distribution of e-g Pairs:
Zipper Library-1 vs Zipper Library-2 Screen
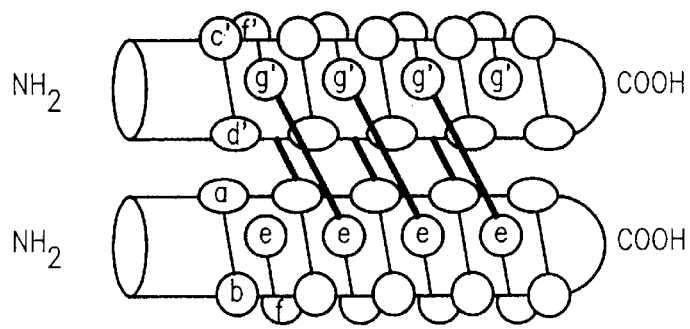
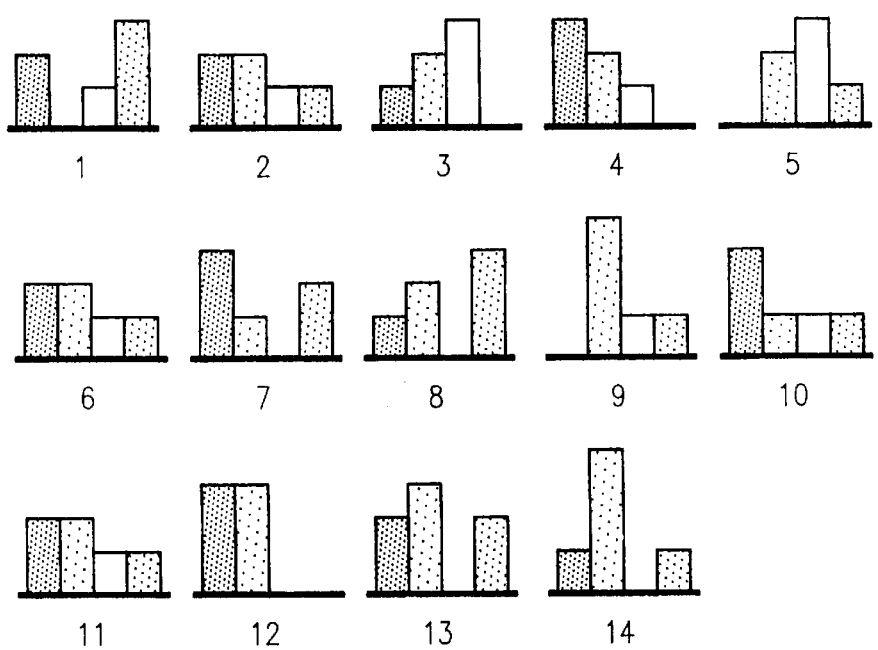
ATTRACTIVE PAIRING        REPULSIVE PAIRING
▓ charge:charge
░ charge:neutral polar     ░ charge:charge
☐ neutral polar:neutral polar

PROTEIN FRAGMENT COMPLEMENTATION ASSAYS FOR THE DETECTION OF BIOLOGICAL OR DRUG INTERACTIONS

This application is a continuation of application Ser. No. 09/017,412 filed Feb. 2, 1998 U.S. Pat. No. 6,270,964.

FIELD OF THE INVENTION

The present invention relates to the determination of the function of novel gene products. The invention further relates to Protein fragment Complementation Assays (PCA). PCAs allow for the detection of a wide variety of types of protein-protein, protein-RNA, protein-DNA, Protein-carbohydrate or protein-small organic molecule interactions in different-cellular contexts appropriate to the study of such interactions.

BACKGROUND OF THE INVENTION

Many processes in biology, including transcription, translation, and metabolic or signal transduction pathways, are mediated by noN-covalently-associated multienzyme complexes[1,101]. The formation of multiprotein or protein-nucleic acid complexes produce the most efficient chemical machinery. Much of modem biological research is concerned with identifying proteins involved in cellular processes, determining their functions and how, when, and where they interact with other proteins involved in specific pathways. Further, with rapid advances in genome sequencing projects there is a need to develop strategies to define "protein linkage maps", detailed inventories of protein interactions that make up functional assemblies of proteins[2,3]. Despite the importance of understanding protein assembly in biological processes, there are few convenient methods for studying protein-protein interactions in viv[4,5]. Approaches include the use of chemical crosslinking reagents and resonance energy transfer between dye-coupled proteins[102,103]. A powerful and commonly used strategy, the yeast two-hybrid system, is used to identify novel protein-protein interactions and to examine the amino acid determinants of specific protein interactions[4,6-8]. The approach allows for rapid screening of a large number of clones, including cDNA libraries. Limitations of this technique include the fact that the interaction must occur in a specific context (the nucleus of *S cerevisiae*), and generally cannot be used to distinguish induced versus constitutive interactions.

Recently, a novel strategy for detecting protein-protein interactions has been demonstrated by Johnsson and Varshavsky[108] called the ubiquitin-based split protein sensor (USPS)[9]. The strategy is based on cleavage of proteins with N-terminal fusions to ubiquitin by cytosolic proteases (ubiquitinases) that recognize its tertiary structure. The strategy depends on the reassembly of the tertiary structure of the protein ubiquitin from complementary N- and C-terminal fragments and crucially, on the augmention of this reassembly by oligomerization domains fused to these fragments. Reassembly is detected as specific proteolysis of the assembled product by cytosolic proteases (ubiquitinases). The authors demonstrated that a fusion of a reporter protein-ubiquitin C-terminal fragment could also be cleaved by ubiquitinases, but only if co-expressed with an N-terminal fragment of ubiquitin that was complementary to the C-terminal fragment. The reconstitution of observable ubiquitinase activity only occurred if the N- and C-terminal fragments were bound through GCN4 leucine zippers[109,110]. The authors suggested that this "split-gene" strategy could be used as an in vivo assay of protein-protein interactions and analysis of protein assembly kinetics in cells. Unfortunately, this strategy requires additional cellular factors (in this case ubiquitinases) and the detection method does not lend itself to high-throughput screening of cDNA libraries.

Rossi, F., C. A. Chariton, and H. M. Blau (1997) Proc. Nat. Acad. Sci. (USA) 94, 8405–8410) have reported an assay based on the classical complementation of α and Ω fragments of β-galactosidase (β-gal) and induction of complementation by induced oligomerization of the proteins FKBP12 and the mamalian target of rapamycin by rapamycin in transfected C2C12 myoblast cell lines. Reconstitution of b-gal activity is detected using substrate fluorescein di-β-D-galactopyranoside using several fluorecence detection assays. While this assay bears some resemblance to the present invention, there are several significant distinguishing differences. First, this particular complementation approach has been used for over thirty years in a vast number of applications including the detection of protein-protein interactions. Krevolin, M. and D. Kates (1993) U.S. Pat. No. 5,362,625) teaches the use of this complementation to detect protein-protein interactions. Also achievement of β-gal complementation in mamalian cells has previously been reported (Moosmann, P. and S. Rusconi (1996) Nucl. Acids Res. 24, 1171–1172). The individual PCAs presented here are completely de novo designed interaction detection assays, not described in any way previously except for publications arising from applicants laboratory. Secondly, this application describes a general strategy to develop molecular interaction assays from a large number of enzyme or protein detectors, all de novo designed assays, whereas the β-gal assay is not novel, nor are any general strategies or advancements over previosly well documented applications given.

As in the USPS, the yeast-two hybrid strategy requires additional cellular machinery for detection that exist only in specific cellular compartments. There is therefore a need for a detection system which uses the reconstitution of a specific enzyme activity from fragments as the assay itself, without the requirement for other proteins for the detection of the activity. Preferably, the assay would involve an oligomerization-assisted complementation of fragments of monomeric or multimeric enzymes that require no other proteins for the detection of their activity. Furthermore, if the structure of an enzyme were known it would be possible to design fragments of the enzyme to ensure that the reassembled fragments would be active and to introduce mutations to alter the stringency of detection of reassembly. However, knowledge of structure is not a prerequesite to the design of complementing fragments, as will be explained below. The flexibility allowed in the design of such an approach would make it applicable to situations where other detection systems may not be suitable.

Recent advances in human genomics research has led to rapid progress in the identification of novel genes. In applications to biological and pharmaceutical research, there is now the pressing need to determine the functions of novel gene products; for example, for genes shown to be involved in disease phenotypes. It is in addressing questions of function where genomics-based pharmaceutical research becomes bogged down and there is now the need for advances in the development of simple and automatable functional assays. A first step in defining the function of a novel gene is to determine its interactions with other gene products in an appropriate context; that is, since proteins make specific interactions with other proteins or other biopolymers as part of functional assemblies, an appropriate way to examine the function of a novel gene is to determine its physical relationships with the products of other genes.

Screening techniques for protein interactions, such as the yeast "two-hybrid" system, have transformed molecular biology, but can only be used to study specific types of constitutively interacting proteins or interactions of proteins with other molecules, in narrowly defined cellular and compartmental contexts and require a complex cellular machinery (transcription) to work. To rationally screen for protein interactions within the context of a specific problem requires more flexible approaches. Specifically, assays that meet criteria necessary not only to detecting molecular interactions, but also to validating these interactions as specific and biologically relevant.

A list of assay characteristics that meet such criteria are as follows:

1) Allow for the detection of protein-protein, protein-DNA/RNA or protein-drug interactions in vivo or in vitro.
2) Allow for the detection of these interactions in appropriate contexts, such as within a specific organism, cell type, cellular compartment, or organelle.
3) Allow for the detection of induced versus constitutive protein-protein interactions (such as by a cell growth or inhibitory factor).
4) To be able to distinguish specific versus non-specific protein-protein interactions by controlling the sensitivity of the assay.
5) Allow for the detection of the kinetics of protein assembly in cells.
6) Allow for screening of cDNA, small organic molecule, or DNA or RNA libraries for molecular interactions.

SUMMARY OF THE INVENTION

The present invention seeks to provide the above-mentioned needs for which the prior art is silent. The present invention provides a general strategy for detecting protein interactions with other biopolymers including other proteins, nucleic acids, carbohydrates or for screening small molecule libraries for compounds of potential therapeutic value. In a preferred embodiment, the instant invention seeks to provide an oligomerization-assisted complementation of fragments of monomeric enzymes that require no other proteins for the detection of their activity. In one such embodiment, a protein-fragment complementation assay (PCA) based on reconstitution of dihydrofolate reductase activity by complementation of defined fragments of the enzyme in *E. coli* is hereby provided. This assay requires no additional endogenous factors for detecting specific protein-protein interactions (i.e. leucine zipper interactions) and can be conveniently extended to screening cDNA, nucleic acid, small molecule or protein design libraries for molecular interactions. In addition, the assay can also be adapted for detection of protein interactions in any cellular context or compartment and be used to distinguish between induced versus constitutive protein interactions in both prokaryotic and eukaryotic systems.

One particular strategy for designing a protein complementation assay (PCA) is based on using the following characteristics: 1) A protein or enzyme that is relatively small and monomeric, 2) for which there is a large literature of structural and functional information, 3) for which simple assays exist for the reconstitution of the protein or activity of the enzyme, both in vivo and in vitro, and 4) for which overexpression in eukaryotic and prokaryotic cells has been demonstrated. If these criteria are met, the structure of the enzyme is used to decide the best position in the polypeptide chain to split the gene in two, based on the following criteria: 1) The fragments should result in subdomains of continuous polypeptide; that is, the resulting fragments will not disrupt the subdomain structure of the protein, 2) the catalytic and cofactor binding sites should all be contained in one fragment, and 3) resulting new N- and C-termini should be on the same face of the protein to avoid the need for long peptide linkers and allow for studies of orientation-dependence of protein binding.

It should be understood that the above mentioned criteria do not all need to be satisfied for a proper working of the present invention. It is an advantage that the enzyme be small, preferably between 10–40 kDa. Although monomeric enzymes are preferred, multimeric enzymes can also be envisaged as within the scope of the present invention. The dimeric protein tyrosinase can be used in the instant assay. The information on the structure of the enzyme provides an additional advantage in designing the PCA, but is not necessary. Indeed, an additional strategy, to develop PCAs is presented, based on a combination of exonuclease digestion-generated protein fragments followed by directed protein evolution in application to the enzyme aminoglycoside kinase. Although the overexpression in prokaryotic cells is preferred it is not a necessity. It will be understood to the skilled artisan that the enzyme catalytic site (of the chosen enzyme) does not absolutely need to be on same molecule.

The present application explains the rationale and criteria for using a particular enzyme in a PCA. FIG. 1 shows a general description of a PCA. The gene for a protein or enzyme is rationally dissected into two or more fragments. Using molecular biology techniques, the chosen fragments are subcloned, and to the 5' ends of each, proteins that either are known or thought to interact are fused. Co-transfection or transformation these DNA constructs into cells is then carried out. Reassembly of the probe protein or enzyme from its fragments is catalyzed by the binding of the test proteins to each other, and reconstitution is observed with some assay. It is crucial to understand that these assays will only work if the fused, interacting proteins catalyze the reassembly of the enzyme. That is, observation of reconstituted enzyme activity must be a measure of the interaction of the fused proteins.

A preferred embodiment of the present invention focuses on a PCA based on the enzyme dihydrofolate reductase. Expansion of the strategy to include assays in eukaryotic, cells, library screening, and a specific application to problems concerning the study of integrated biochemical pathways such as signal transduction pathways, is presented. Additional assays, including those based on enzymes that can act as dominant or recessive drug selection or metabolic salvage pathways are disclosed. In addition, PCAs based on enzymes that will produce a colored or fluorescent product are also disclosed. The present invention teaches how the PCA strategy can be both generalized and automated for functional testing of novel genes, screening of natural products or compound libraries for pharmacological activity and identification of novel gene products that interact with DNA, RNA or carbohydrates are disclosed. It also teaches how the PCA strategy can be applied to identifying natural products or small molecules from compound libraries of potential therapeutic value that can inhibit or activate such molecular interactions and how enzyme substrates and small molecule inhibitors of enzymes can be identified. Finally, it teaches how the PCA strategy can be used to perform protein engineering experiments that could lead to designed enzymes with industrial applications or peptides with biological activity.

Simple strategies to design and implement assays for detecting protein interactions in vivo are disclosed herein. We have designed complementary fragments of the native mDHFR that, when coexpressed in *E. coli* grown in minimal medium, allow for survival of clones expressing the two fragments, where the basal activity of the endogenous bacterial DHFR is inhibited by the competitive inhibitor trimethoprim (FIG. 3). Reconstitution of activity only occurred when both N- and C-terminal fragments of DHFR were coexpressed as C-terminal fusions to GCN4 leucine zipper sequences, indicating that reassembly of the fragments requires formation of a leucine zipper between the N- and C-terminal fusion peptides. The sequential increase in cell doubling times resulting from the destabilizing mutations directed at the assembly interface (Ile114 to Val, Ala or Gly) demonstrates that the observed cell survival under selective conditions is a result of the specific, leucine-zipper-assisted association of mDHFR fragment[1,2] with fragment[3], as opposed to nonspecific interactions of Z-F[3] with Z-F[1,2]. several detailed and many additional examples are given.

As demonstrated previously with the ubiquitin-based split protein sensor (USPS)[9], a protein-fragment complementation strategy can be used to study equilibrium and kinetic aspects of protein-protein interactions in vivo. The DHFR and other PCAs however, are simpler assays. They are complete systems; no additional endogenous factors are necessary and the results of complementation are observed directly, with no further manipulation. The *E. coli* cell survival assay described herein should therefore be particularly useful for screening cDNA libraries for protein-protein interactions. mDHFR expression in cells can be monitored by binding of fluorescent high-affinity substrate analogues for DHFR[26].

There are several further aspects of the PCAs that distinguish them from all other strategies for studying protein-protein interactions in vivo (except USPS). We have designed complementary fragments of enzymes that allow for controlling the stringency of the assay, and could be used to obtain estimates of the kinetics and equilibrium constants for association of two proteins. For example, with DHFR the point mutations of the wild-type enzyme Ile 114 to Val, Ala, or Gly alter the stringency of reconstitution of DHFR activity. For determining estimates of equilibrium and kinetic parameters for a specific protein-protein interaction, one could perform a series of DHFR PCA experiments with two proteins that interact with a known affinity, using the wild type or destabilizing mutant DHFR fragments. Comparison of cell growth rates in this model system with rates for a DHFR PCA using unknowns would give an estimate of the strength of the unknown interaction.

It should be understood that the present invention should not be limited to the DHFR or other PCAs presented, as it is only non-limiting embodiments of the protein complementation assay of the present invention. Moreover, the PCAs should not be limited in the context in which they could be used. Constructs could be designed for targeting the PCA fusions to specific compartments in the cell by addition of signaling peptide sequences[27,28]. Induced versus constitutive protein-protein interactions could be distinguished by a eukaryotic version of the PCA, in the case of an interaction that is triggered by a biochemical event. Also, the system could be adapted for use in screening for novel, induced protein-molecular associations between a target protein and an expression library.

The instant invention is also directed to a method for detecting biomolecular interactions said method comprising:
(a) selecting an appropriate reporter molecule;
(b) effecting fragmentation of said reporter molecule such that said fragmentation results in reversible loss of reporter function;
(c) fusing or attaching fragments of said reporter molecule separately to other molecules; followed by
(d) reassociation of said reporter fragments through interactions of the molecules that are fused to said fragments.

The invention also provides molecular fragment complementation assays for the detection of molecular interactions comprising a reassembly of separate fragments of a molecule, wherein reassembly of said fragments is operated by the interaction of molecular domains fused to each fragment of said molecules, and wherein reassembly of the fragments is independent of other molecular processes.

In another aspect, the present invention is directed to a method of testing biomolecular interactions comprising:
a) generating a first fusion product comprising
   i) a first fragment of a first molecule and
   ii) a second molecule which is different or the same as said first molecule;
b) generating a second fusion product comprising
   i) a second fragment of said first molecule; and
   ii) a third molecule which is different from or the same as said first molecule or second molecule;
c) allowing the first and second fusion products to contact each other; and
d) testing for activity regained by association of the recombined fragments of the first molecule, wherein said reassociation is mediated by interaction of the second and third molecules.

In another novel feature, the invention is directed to a method comprising an assay where fragments of a first molecule are fused to a second molecule and fragment association is detected by reconstitution of the first molecule's activity.

The present invention also provides a composition comprising a product selected from the group consisting of:
(a) a first fusion product comprising:
   1) a first fragment of a first molecule whose fragments can exhibit a detectable activity when associated and
   2) a second molecule that can bind (a)(1);
(b) a second fusion product comprising
   1) a second fragment of said first molecule and
   2) a third molecule that can bind (b)(1); and
c) both (a) and (b).

The invention further provides a composition comprising complementary fragments of a first molecule, each fused to a separate fragment of a second molecule.

The inventors of the present subject matter further provide a composition comprising a nucleic acid molecule coding for a fusion product, which molecule comprises sequences coding for a product selected from the group consisting of:
(a) a first fusion product comprising:
   1) fragments of a first molecule whose fragments can exhibit a detectable activity when associated and
   2) a second molecule fused to the fragment of the first molecule;
(b) a second fusion product comprising
   1) a second fragment of said first molecule and
   2) a second or third molecule; and
(c) both (a) and (b).

The present invention is also directed to a method of testing for biomolecular interactions associated with: (a) complementary fragments of a first molecule whose fragments can exhibit a detectable activity when associated or (b) binding of two protein-protein interacting domains from a second or third molecule, said method comprising:

1) creating a fusion of
   (a) a first fragment of a first molecule whose fragments can exhibit a detectable activity when associated and
   (b) a first protein-protein interacting domain;
2) creating a fusion of
   (a) a second fragment of said first molecule and
   (b) a second protein-protein interacting domain that can bind said first protein-protein interacting domain;
3) allowing the fusions of (1) and (2) to contact each other; and
4) testing for said activity.

The instant invention further provides a composition comprising a product selected from the group consisting of:
   (a) a first fusion product comprising:
      1) a first fragment of a molecule whose fragments can exhibit a detectable activity when associated and
      2) a first protein-protein interacting domain;
   (b) a second fusion product comprising
      1) a second fragment of said first molecule and
      2) a second protein-protein interacting domain that can bind said first protein-protein interacting domain; and
   (c) both (a) and (b).

The invention is also directed to a composition comprising a nucleic acid molecule coding for a fusion product, which molecule comprises sequences coding for either:
   (a) a first fusion product comprising:
      1) a first fragment of a molecule whose fragments can exhibit a detectable activity when associated and
      2) a first protein-protein interacting domain; or
   (b) a second fusion product comprising
      1) a second fragment of said molecule and
      2) a second protein-protein interacting domain that can bind said first protein-protein interacting domain; or
   (c) both (a) and (b).

The invention also provides a method of detecting kinetics of protein assembly and screening cDNA libraries comprising performing PCA.

In another embodiment, the invention further provides a method of testing the ability of a compound to inhibit molecular interactions in a PCA comprising performing a PCA in the presence of said compound and correlating any inhibition with said presence.

In a further embodiment, the invention provides a method for detecting protein-protein interactions in living organisms and or cells, which method comprises:
   (a) synthesizing probe protein fragments from an enzyme which enables dominant selection by dissecting the gene coding for the enzyme into at least two fragments;
   (b) constructing fusion proteins with one or more molecules that are to be tested for interactions;
   (c) fusing the proteins obtained in (b) with one or more of the probe fragments;
   (d) coexpressing the fusion proteins; and
   (e) detecting the reconstitution of enzyme activity.

The invention still provides a method for detecting biomolecular interactions said method comprising:
   (a) selecting an appropriate reporter molecule;
   (b) effecting fragmentation of said reporter molecule;
   (c) fusing or attaching fragments of said reporter molecule separately to other molecules; followed by
   (d) reassociation of said reporter fragments through interactions of the molecules that are fused to said fragments.

Lastly, the invention also provides a novel method of affecting gene therapy, which includes the step of providing the assays and compositions described above.

The present invention is pionneering as it is the first protein complementation assay displaying such a level of simplicity and versatility. The exemplified embodiments are protein-fragment complementation assays (PCA) based on mDHFR, where a leucine zipper directs the reconstitution of DHFR activity. Activity was detected by an $E.$ $coli$ survival assay which is both practical and inexpensive. This system illustrates the use of mDHFR fragment complementation in the detection of leucine zipper dimerization and could be applied to the detection of unknown, specific protein-molecular interactions in vivo.

It should be undertstood that the instant invention is not limited to the PCAs presented here, as numerous other enzymes can be selected and used in accordance with the teachings of the present invention. Examples of such markers can be found in Kaufman, (1987 Genetic Eng. 9:155–198) and references found therein as well as table 1 of this application.

It should also be clear to the skilled artisan to which the present invention pertains that the invention is not limited to the use of leucine zippers as the two interacting molecules. Indeed, numerous other types of protein-molecule interactions can be used and identified in accordance with the teaching of the present invention. The known types of motifs involved in protein-molecular interactions are well known in the art.

The present application refers to numerous prior art documents and the entire contents of all those prior art documents are herein incorporated by reference.

Other features and advantages of the present invention will be apparent from the following description of the preferred embodiments thereof, the appended Examples and from the enjoined claims.

(B) *E. coil* survival assay using destabilizing DHFR mutants. Panel I: Cotransformation of *E. coli* with constructs Z-F[1,2] and Z-F[3:Ile114Val]. Panel II: Cotransformation with Z-F[1,2] and Z-F[3:Ile114Ala]. Inset is a 5-fold enlargement of the right-side plate. Panel III: Cotransformation with Z-F[1,2] and Z-F[3:Ile 114Gly]. All plates contain 0.5 mg/ml trimethoprim. Plates on the right side contain 1 mM IPTG.

Figure 4A:
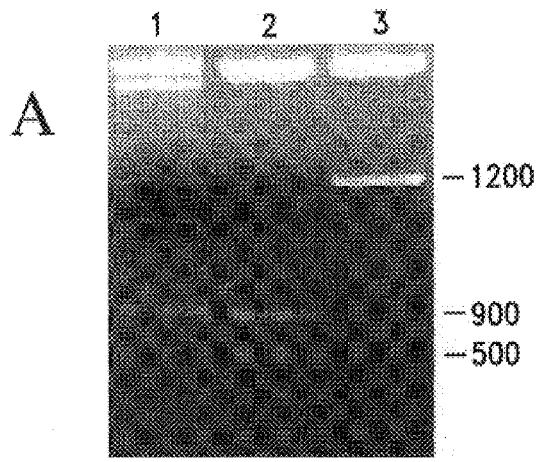

FIG. 4 features the coexpression of mDHFR fragments. (A) Agarose gel analysis of restriction pattern resulting from Hincl digestion of plasmid DNA. Lane 1 contains DNA isolated from *E. coli* cotransformed with constructs Z-F[1,2] and Z-F[3]. Lanes 2 and 3 contain DNA isolated from *E. coli* transformed with, respectively, construct Z-F[3] and construct Z-F[1,2]. Fragment migration (in bp) is indicated to the right.

(B) SDS-PAGE analysis of mDHFR fragment expression. Lanes 1 to 5 show crude lysate of untransformed *E. coli* (lane 1), or *E. coli* expressing Z-F[1,2] (20.8 kDa; lane 2), Z-F[3] (18.4 kDa; lane 3), Control-F[1,2] (14.2 kDa; lane 4), and Z-F[1,2]+Z-F[3] (lane 5). Lane 6 shows 40 ml out of 2ml copurified Z-F[1,2] and Z-F[3]. Arrowheads point to the proteins of interest. Migration of molecular weight markers (in kDa) is indicated to the right.

FIG. 5 illustrates the general features of a PCA based on a survival assay such as the DHFR PCA. The assay can be used in a bacterial or a mammalian context. The inserted target DNA can be a known sequence coding for a protein (or protein domain) of interest, or can be a cDNA library.

Figure 6:
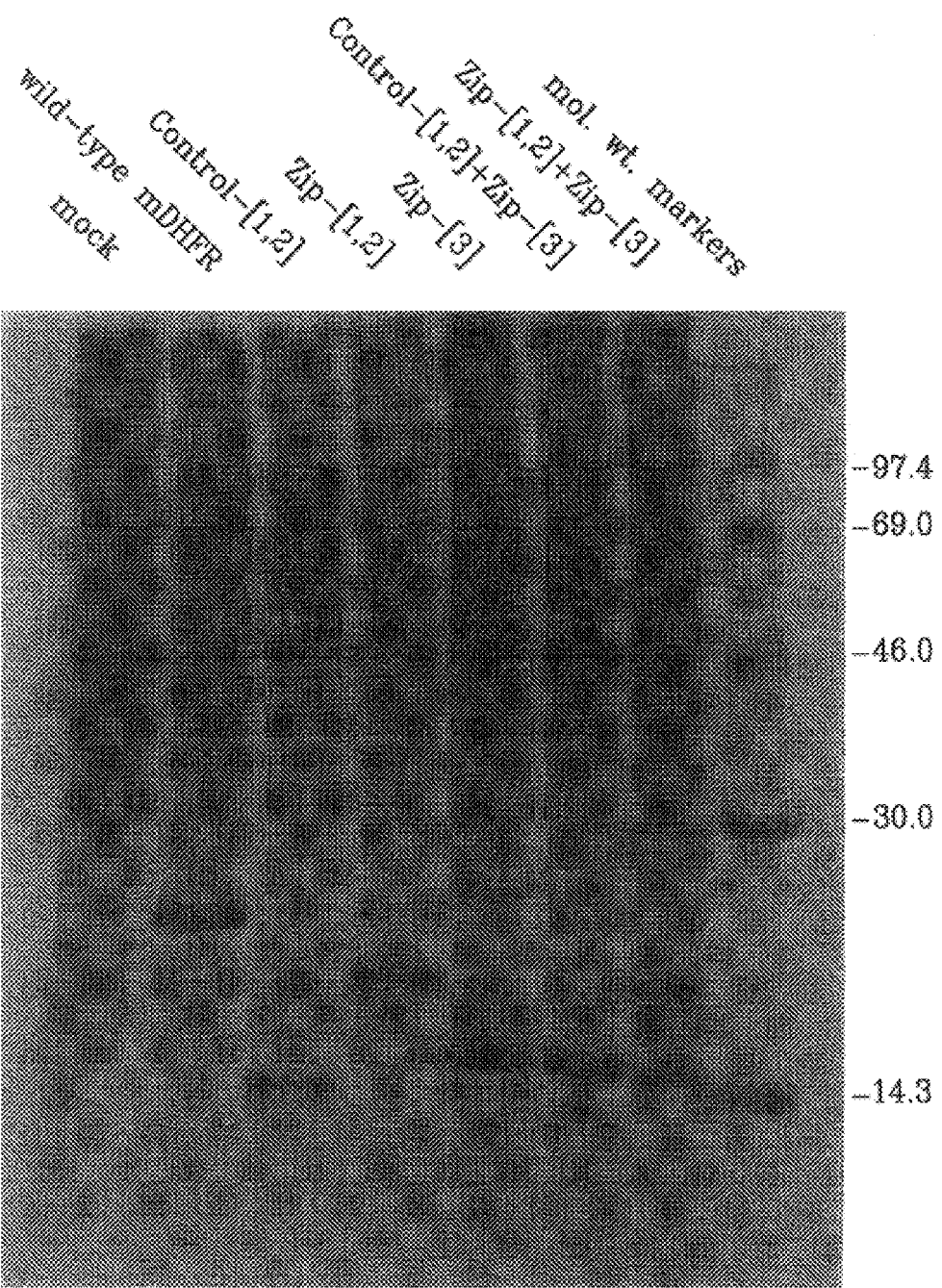

FIG. 6 represents an autoradiograph of a COS cell lysate after a 30 min. $^{35}$S-Met-Cys pulse-labelling. The expression pattern is essentially identical to that observed in *E. coli* (see FIG. 4). The DNA transfected into the cells (or cotransfected) is indicated above the respective lanes.

FIG. 7 illustrates the results of a protein engineering application of the mDHFR bacterial PCA. Two semi-random leucine zipper libraries were created (as described in the text) and each inserted N-terminal to one of the mDHFR fragments. Cotransformation of the resulting zipper-DHFR fragment libraries in *E. coli* and plating on selective medium allowed for survival of clones harboring successfully interacting leucine zippers. Fourteen clones were isolated and the zippers were sequenced to identify the residues at the "e" and "g" positions. The "e–g" pairs were categorized, as having attractive pairing (charge:charge, charge:neutral polar or neutral polar:neutral polar) or repulsive pairing (charge:charge) and the number of each type of interaction scored for each clone. The total number of interactions for each clone is 6; the interactions are tallied on the histogram.

Other objects, advantages and features of the present invention will become more apparent upon reading of the following non-restrictive description of preferred embodiments with reference to the accompanying drawings which are examplary and should not be interpreted as limiting the scope of the present invention.

DESCRIPTION OF THE PREFERRED EMBODIMENTS

Selection of mDHFR for a PCA.

In designing a protein-fragment complementation assay (PCA), we sought to identify an enzyme for which the following is true: 1) An enzyme that is relatively small and monomeric, 2) for which structural and functional information exists, 3) for which simple assays exist for both in vivo and in vitro measurement, and 4) for which overexpression in eukaryotic and prokaryotic cells has been demonstrated.

Murine DHFR (mDHFR) meets all of the criteria for a PCA listed above. Prokaryotic and eukaryotic DHFR is central to cellular one-carbon metabolism and is absolutely required for cell survival in both prokaryotes and eukaryotes. Specifically it catalyses the reduction of dihydrofolate to tetrahydrofolate for use in transfer of one-carbon units required for biosynthesis of serine, methionine, purines and thymidylate. The DHFRs are small (17 kD to 21 kD), monomeric proteins. The crystal structures of DHFR from various bacterial and eukaryotic sources are known and substrate binding sites and active site residues have been determined [111-114], allowing for rational design of protein fragments. The folding, catalysis, and kinetics of a number of DHFRs have been studied extensively[115-119]. The enzyme activity can be monitored in vitro by a simple spectrophotometric assay[120], or in vivo by cell survival in cells grown in the absence of DHFR end products. DHFR is specifically inhibited by the anti-folate drug trimethoprim. As mammalian DHFR has a 12000-fold lower affinity for trimethoprim than does bacterial DHFR[121], growth of bacteria expressing mDHFR in the presence of trimethoprim levels lethal to bacteria is an efficient means of selecting for reassembly of mDHFR fragments into active enzyme. High level expression of mDHFR has been demonstrated in transformed prokaryote or transfected eukaryotic cells[122-126].

Design Considerations.

mDHFR shares high sequence identity with the human DHFR (hDHFR) sequence (91% identity) and is highly homologous to the *E. coli* enzyme (29% identity, 68% homology) and these sequences share visually superimposable tertiary structure[111]. Comparison of the crystal structures of mDHFR and hDHFR suggests that their active sites are essentially identical[127,128]. DHFR has been described as being formed of three structural fragments forming two domains[129,130] the adenine binding domain (residues 47 to 105=fragment[2]) and a discontinuous domain (residues 1 to 46=fragment[1] and 106 to 186 [3]; numbering according to the murine sequence). The folate binding pocket and the NADPH binding groove are formed mainly by residues belonging to fragments[1] and [2]. Fragment [3] is not directly implicated in catalysis.

Residues 101 to 108 of hDHFR, at the junction between fragment[2] and fragment[3], form a disordered loop which lies on the same face of the protein as both termini. We chose to cleave mDHFR between fragments [1,2] and [3], at residue 107, so as to cause minimal disruption of the active site and NADPH cofactor binding sites. The native N-terminus of mDHFR and the novel N-terminus created by cleavage occur on the same surface of the enzyme[112,128] allowing for ease of N-terminal covalent attachment of each fragment to associating fragments such as the leucine zippers used in this study. Using this system, we have obtained leucine-zipper assisted assembly of the mDHFR fragments into active enzyme.

EXAMPLE 1

EXPERIMENTAL PROTOCOL

DNA Constructs.

Figure 1:
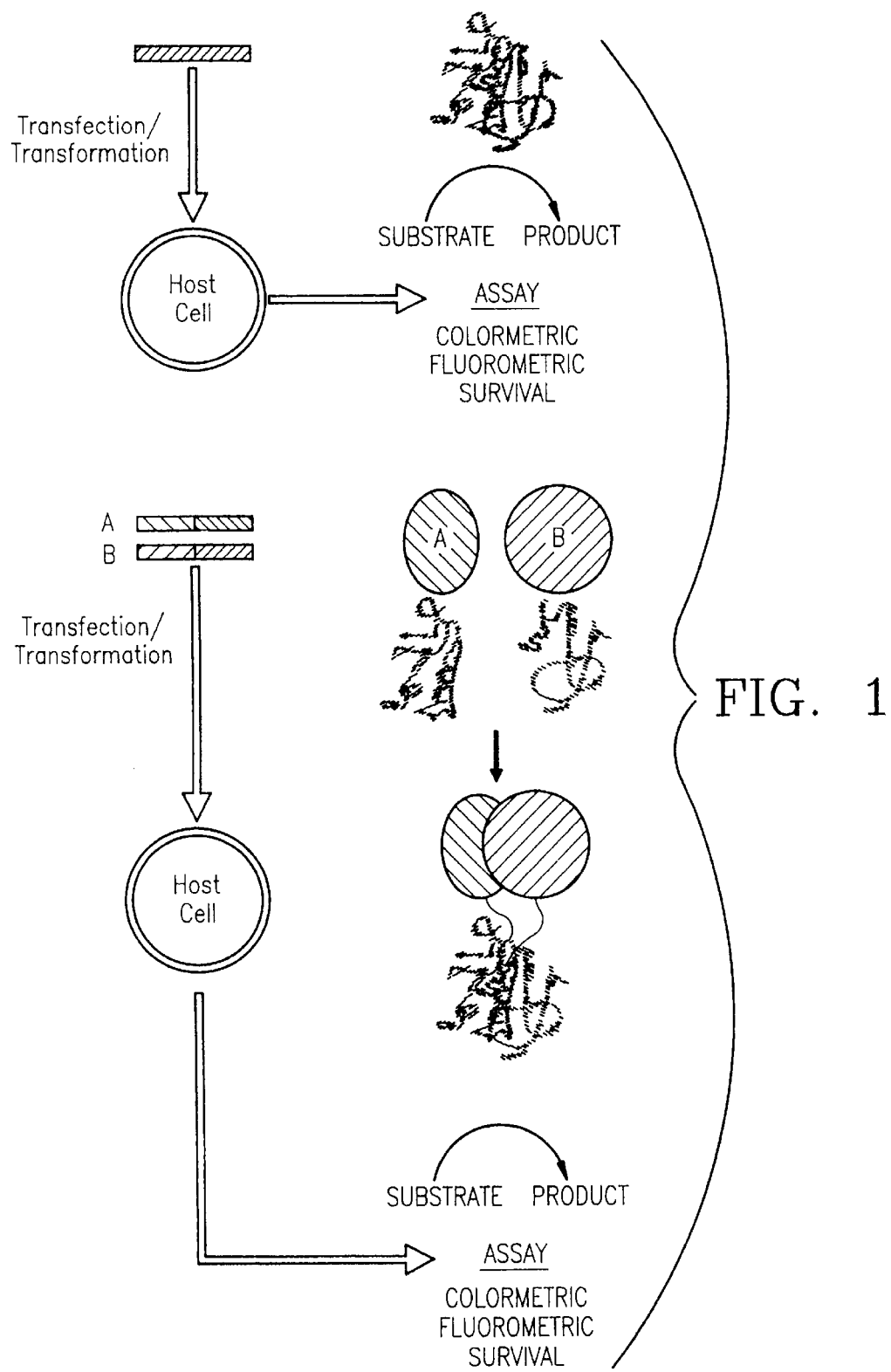
FIG. 1 provides a general description of a PCA. Using molecular biology techniques, the chosen fragments of the enzyme are subcloned, and to the 5' ends of each, proteins that either are known or thought to interact are fused. Co-transfection or transformation these DNA constructs into cells is then carried out and reconstitution with some assay is observed.
Figure 2:
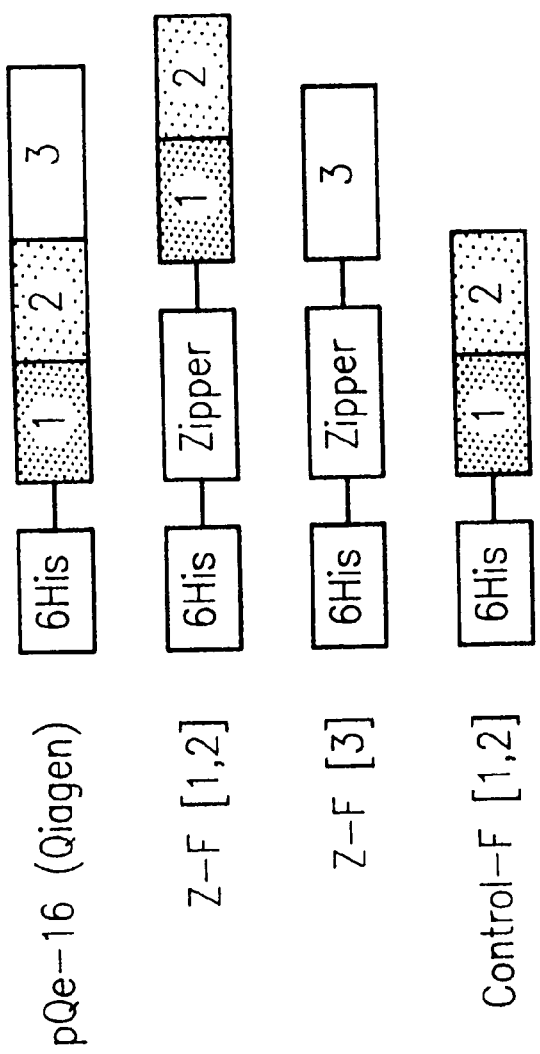
FIG. 2 is a scheme of the fusion constructs used in one of the embodiments of the invention. The hexahistidine peptide (6His), the homodimerizing GCN4 leucine zipper (Zipper) and mDHFR fragments (1, 2 and 3) are illustrated. The labels for the constructs are used to identify both the DNA constructs and the proteins expressed from these constructs.

Mutagenic and sequencing oligonucleotides were purchased from Gibco BRL. Restriction endonucleases and DNA modifying enzymes were from Pharmacia and New England Biolabs. The mDHFR fragments carrying their own iN-frame stop codon were subcloned into pQE-32 (Qiagen), downstream from and iN-frame with the hexahistidine peptide and a GCN4 leucine zipper (FIG. 1; FIG. 2). All final constructs were based on the Qiagen pQE series of vectors, which contain an inducible promoter-operator element (tac), a consensus ribosomal binding site, initiator codon and nucleotides coding for a hexahistidine peptide. Full-length mDHFR is expressed from pQE-16 (Qiagen).

Expression vector harboring the GCN4 leucine zipper Residues 235 to 281 of the GCN4 leucine zipper (a SalI/BamHI 254 bp fragment) were obtained from a yeast expression plasmid pRS316[9]. The recessed terminus at the BamHI site was filled-in with Klenow polymerase and the fragment was ligated to pQE-32 linearized with SalI/HindIII(filled-in). The product, construct Z, carries an open reading frame coding for the sequence Met-Arg-Gly-Ser followed by a hexahistidine tag and 13 residues preceding the GCN4 leucine zipper residues.

Creation of DHFR fragments:

The eukaryotic transient expression vector, pMT3 (derived from pMT2)[16], was used as a template for PCR-generation of mDHFR containing the features allowing subcloning and separate expression of fragment[1,2] and fragment[3]. The megaprimer method of PCR mutagenesis[29] was used to generate a full-length 590 bp product. Oligonucleotides complementary to the nucleotide sequence coding for the N- and C-termini of mDHFR and containing a novel BspEI site outside the coding sequence were used as well as an oligonucleotide used to create a novel stop codon after fragment[1,2], followed by a novel SpeI site for use in subcloning fragment[3].

Construction of a new multiple cloning region and subcloning of DHFR fragments [1,2] and [3]

Complementary oligonucleotides containing the novel restriction sites: SnaBI, NheI, SpeI and BspEI, were hybridized together resulting in 5' and 3' overhangs complementary to EcoRI, and inserted into pMT3 at a unique EcoRI site. The 590 bp PCR product (described above) was digested with BspEI and inserted into pMT3 linearized at BspEI, yielding construct [1,2,3]. The 610 bp BspEI/EcoNI fragment (coding for DHFR fragment[1,2], followed by a novel stop and fragment[3] up to EcoNI) was filled in at EcoNI and subcloned into pMT3 opened with BspEI/HpaI, yielding construct F[1,2]. The 250 bp SpeI/BspEI fragment of construct [1,2,3] coding for DHFR fragment[3] (with no in-frame stop codon) was subcloned into pMT3 opened with the same enzymes. The stop codon of the wild-type DHFR sequence, downstream from fragment[3] in pMT3, was inserted as follows. Cleavage with EcoNI, present in both the inserted fragment[3] and the wild-type fragment[3], removal of the 683 bp intervening sequence and religation of the vector yielded a construct of fragment[3] with the wild-type stop codon, construct F[3].

Creation of the expression constructs

The 1051 bp and the 958 bp SnaBI/XbaI fragments of constructs F[1,2] and F[3], respectively, were subcloned into construct Z opened with BglII(filled-in)/NheI, yielding constructs Z-F[1,2] and Z-F[3] (FIG. 2). For the Control expression construct, the 180 bp XmaI/BspEI fragment coding for the zipper was removed from construct Z-F[1,2], yielding construct Control-F[1,2] (FIG. 2).

Creation of Stability Mutants

Site-directed mutagenesis was performed[3] to produce mutants at Ile 114 (numbering of the wild-type mDHFR). The mutagenesis reaction was carried out on the KpnI/BamHI fragment of construct Z-F[3] subcloned into pBluescript SK+ (Stratagene), using oligonucleotides that encode a silent mutation producing a novel BamHI site. The 206 bp NheI/EcoNI fragment of putative mutants identified by restriction was subcloned back into Z-F[3]. The mutations were confirmed by DNA sequencing.

*E. coli* Survival Assay

*E. coli* strain BL21 carrying plasmid pRep4 (from Qiagen, for constitutive expression of the lac repressor) were made competent, transformed with the appropriate DNA constructs and washed twice with minimal medium before plating on minimal medium plates containing 50 mg/ml kanamycin, 100 mg/ml ampicillin and 0.5 mg/ml trimethoprim. One half of each transformation mixture was plated in the absence, and the second half in the presence, of 1 mM IPTG. All plates were placed at 37° C. for 66 hrs.

*E. coli* Growth Curves

Colonies obtained from cotransformation were propagated and used to inoculate 10 ml of minimal medium supplemented with ampicillin, kanamycin as well as IPTG (1mM) and trimethoprim (1 $\mu g/\mu l$) where indicated. Cotransformants of Z-F[1,2]+Z-F[3:Ile 114Gly] were obtained under non-selective conditions by plating the transformation mixture on L-agar (+kanamycin and ampicillin) and screening for the presence of the two constructs by restriction analysis. All growth curves were performed in triplicate. Aliquots were withdrawn periodically for measurement of optical density. Doubling time was calculated for early logarithmic growth (OD 600 between 0.02 and 0.2).

Protein Overexpression and Purification

Bacteria were propagated in Terrific Broth[31] in the presence of the appropriate antibiotics to an OD600 of approximately 1.0. Expression was induced by addition of 1 mM IPTG and further incubation for 3 hrs. For analysis of crude extract, pellets from 150 ml of induced cells were lysed by boiling in loading dye. The lysates were clarified by microcentrifugation and analyzed by SDS-PAGE32. For protein purification, a cell pellet from 50 ml of induced *E. coli* cotransformed with constructs Z-F[1,2] and Z-F[3] was lysed by sonication, and a denaturing purification of the insoluble pellet undertaken using Ni-NTA (Qiagen) as described by the manufacturer. The proteins were eluted with a stepwise imidazole gradient. The fractions were analyzed by SDS-PAGE.

RESULTS

Figure 3A:
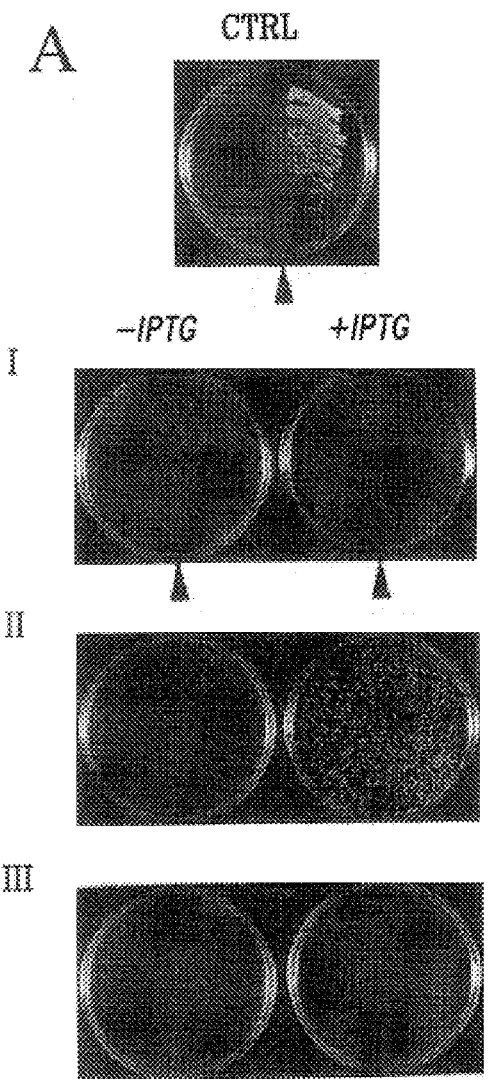
FIG. 3: (A) shows $E.$ $coli$ survival assay on minimal medium plates. Control: Left side of the plate: $E.$ $coli$ harboring pQE-30 (no insert); right side: $E.$ $coli$ harboring pQE-16, coding for native mDHFR. Panel I: Left side of each plate: transformation with construct Z-F[1,2]; right side of each plate: transformation with construct Z-F[3]. Panel II: Cotransformation with constructs Z-F[1,2] and Z-F[3]. Panel III: Cotransformation with constructs Control-F[1,2] and Z-F[3]. All plates contain 0.5 mg/ml trimethoprim. In panels I to III, plates on the right side contain 1 mM IPTG.

Design of mDHFR fragments for a PCA mDHFR shares high sequence identity with the human DHFR (hDHFR) sequence. As the coordinates of the murine crystal structure were not available, we based our design considerations on the hDHFR structure. DHFR has been described as comprising three structural fragments forming two domains: the adenine binding domain (F[2]) and a discontinuous domain (F[1] and F[3])[13,18]. The folate binding pocket and the NADPH binding groove are formed mainly by residues belonging to F[1] and F[2]. Residues 101 to 108 of hDHFR form a disordered loop which lies on the same face of the protein as both termini. This loop occurs at the junction between F[2] and F[3]. By cleaving mDHFR at residue 107, we created F[1,2] and F[3], thus causing minimal disruption of the active site and substrate binding sites. The native N-terminus of mDHFR and the novel N-terminus created by cleavage were covalently attached to the C-termini of GCN4 leucine zippers (FIG. 1). *E. coli* Survival Assays FIG. 2 illustrates the general features of the expressed constructs and the nomenclature used in this study. FIG. 3 (panel A) illustrates the results of cotransformation of bacteria with constructs coding for Z-F[1,2] and Z-F[3], in the presence of trimethoprim, clearly showing that colony growth under selective pressure is possible only in cells expressing both fragments of mDHFR. There is no growth in the presence of either Z-F[1,2] or Z-F[3] alone. Induction of protein expression with IPTG is essential for colony growth (FIG. 3A). The presence of the leucine zipper on both fragments of mDHFR is essential as illustrated by cotransformation of bacteria with both vectors coding for mDHFR fragments, only one of which carries a leucine zipper (FIG. 3A). It should be noted that growth of control E. coli transformed with the full-length mDHFR is possible in the absence of IPTG due to low levels of expression in uninduced cells.

Figure 4B:
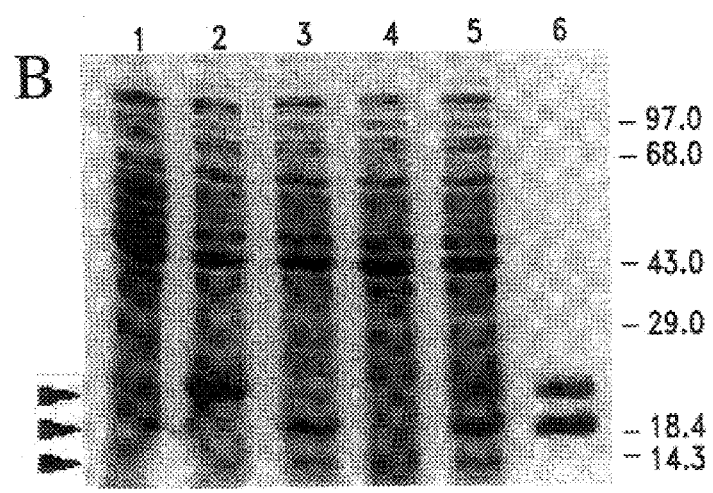

Confirmation of the presence of both plasmids in bacteria able to grow with trimethoprim was obtained from restriction analysis of the plasmid DNA purified from isolated colonies. FIG. 4 (A) reveals the presence of the 1200 bp HincII restriction fragment from construct Z-F[1,2] as well as the 487 and 599 bp HincII restriction fragments from construct Z-F[3]. Also present is the 935 bp HincII fragment of pRep4. Overexpression of the fusion proteins is illustrated in FIG. 4 (B). In all cases, overexpression of a protein of the expected molecular weight is apparent on SDS-PAGE of the crude lysate. Purification of the coexpressed proteins under denaturing conditions yielded two bands of apparent homogeneity upon analysis by Coomassie-stained SDS-PAGE (FIG. 4B).

Stability Mutants

Figure 3B:
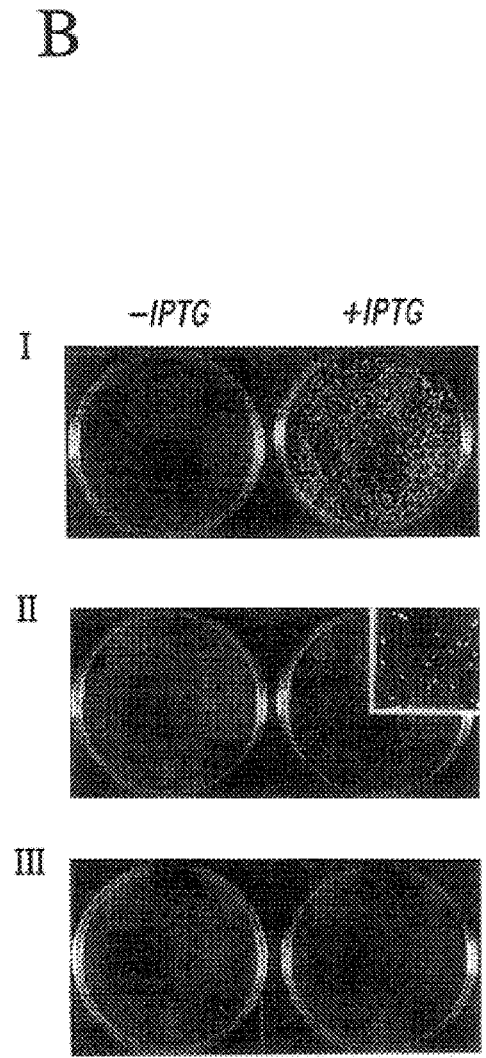

Applicants generated mutants of F[3] to test whether reconstitution of mDHFR activity by fragment assembly was specific. Protein stability can be reduced by changing the side-chain volume in the hydrophobic core of a proteins[9], [22-25]. Residue Ile114 of mDHFR occurs in a core β-strand at the interface between F[1,2] and F[3], isolated from the active site. Ile 114 is in van der Waals contact with Ile51 and Leu93 in F[1,2][11]. We mutated Ile 114 to Val, Ala, or Gly. FIG. 3 (panel B) illustrates the results of cotransformation of E. coli with construct Z-F[1,2] and the mutated Z-F[3] constructs. The colonies obtained from cotransformation with Z-F[3:Ile114Ala] grew more slowly than those cotransformed with Z-F[3] or Z-F[3:Ile 114Val] (see inset to FIG. 3B). No colony growth was detected in cells cotransformed with Z-F[3:Ile114Gly]. The number of transformants obtained was not significantly different in the case where colonies were observed, implying that cells cotransformed with Z-F[1,2] and either Z-F[3], Z-F[3:Ile114Val] or Z-F[3:Ile114Ala] have an equal survival rate. Overexpres of the mutants Z-F[3:Ile114X] was in the same range as Z-F[3], as determined by Coomassie-stained SDS-PAGE (data not shown).

We also compared the relative efficiency of reassembly of mDHFR fragments by measuring the doubling time of the cotransformants in liquid medium. Doubling time in minimal medium was constant for all transformants (data not shown). Selective pressure by trimethoprim in the absence of IPTG prevented growth of E. coli except when transformed with pQE-16 coding for full-length DHFR due to low levels of expression in uninduced cells. Induction of mDHFR fragment expression with IPTG allowed survival of cotransformed cells (except in the case of Z-F[1,2] +Z-F[3:Ile 114Gly], although the doubling times were significantly increased relative to growth in the absence of trimethoprim. The doubling time measured for cells expressing Z-F[1,2]+Z-F[3], Z-F[1,2]+Z-F[3:Ile 114Val] and Z-F[1,2]+Z-F[3:Ile114Ala] were 1.6-fold, 1.9-fold and 4.1-fold, higher respectively, than the doubling time of E. coli expressing pQE-16 in the absence of trimethoprim and IPTG. The presence of IPTG unexpectedly prevented growth of E. coli transformed with full-length mDHFR. Growth was partially restored by addition of the folate metabolism end-products thymine, adenine, pantothenate, glycine and methionine (data not shown). This suggests that induced overexpression of mDHFR was lethal to E. coli when grown in minimal medium as a result of depletion of the folate pool by binding to the enzyme.

In another embodiment, applicants make point mutations in the GCN4 leucine zipper of Z-F[1,2] and Z-F[3], for which direct equilibrium and kinetic parameters are known and correlating these known values with parameters derived from the PCA (Pelletier and Michnick, in preparation). Comparison of cell growth rates in this model system with rates for a DHFR PCA using unknowns would give an estimate of the strength of the unknown interaction. This should enable the determination of estimates of equilibrium and kinetic parameters for a specific protein-protein interaction.

The present invention has illustrated and demonstrated a protein-fragment complementation assay (PCA) based on mDHFR, where a leucine zipper directs the reconstitution of DHFR activity. Activity was detected by an E. coli survival assay which is both practical and inexpensive. This system illustrates the use of mDHFR fragment complementation in the detection of leucine zipper dimerization and could be applied to the detection of unknown, specific protein-protein interactions in vivo.

E coli Aminoglycoside kinase: Optimization and Design of a PCA using an Exonuclease-Molecular Evolution Strategy Although applicants have demonstrated that the engineering/design strategy described above can be used to produce complementary enzyme fragments, it is obvious that proteins did not evolve in such a way that such fragments would be expected to have optimal physical characteristics, including solubility, foldability (fast folding), protease resistance, or enzymatic activity. An alternative embodiment to the engineering/design strategy is the endonuclease/evolution approach. This strategy can be used by itself or in conjunction with the engineering/design strategy. The advantages of this approach are that in principle, prior knowledge of the protein strucuture is not necessary, that the optimal fragments are chosen for PCA and that these fragments will also have optimal characteristics. Following selection of optimal complementary fragments, the fragments are exposed to multiple rounds of random mutagenesis. Mutagenesis is acheived by suboptimal PCR combined with chemical mutagenesis or DNA shuffling (Stemmer, W. P. C. (1994) Proc, Natl, Acad, Sci. USA 91, 10747–10751). The overall strategy is described for the case of aminoglycoside kinase (AK), an example of antibiotic resistance marker that can be used for dominant selection of prokaryotic cells such as E. coli or eukaryotic cells such as yeast or mammalian cell lines. The structure of an AK is already known, and so strategy (1) would be possible, however we chose to combine both strategy (1) as defined for DHFR above, in conjunction with strategy (2).

EXPERIMENTAL PROTOCOL

The optimization/selection procedure is as follows:
Generation of of library of AK fragments based on products of Exonuclease digestion Nested sets of deletions are created at the 5' and the 3' ends of the AK gene. In order to create unidirectional deletions, unique restriction sites are introduced in the regions flanking the AK gene. At the 5' and 3' termini, an "outer" sticky site with a protruding 3' terminus (Sph I and Kpn I, respectively) and an "inner" sticky site with recessed 3' terminus (Bgl II and Sal I, respectively) are added by PCR. Cleavage at Sph I and Bgl II (or Kpn I and Sal I) results in creation of a protruding terminus leading back to the flanking sequence and a recessed terminus leading into the AK gene. Digestion with E. coli exonuclease III and S1 nuclease (Henikoff, S. (1987) Methods in Enzymology 155, 156–165) yields a set of nested deletions from the recessed terminus only. Thus, 10 mg of DNA is digested with Sph I and Bgl II (or Kpn I and Sal I), phenol-chloroform extracted, and 12.5 U exonuclease III added. At 30 sec intervals over 10 min, aliquots are taken and put into solution with 2 U S1 nuclease. The newly created ends are filled in with T4 DNA polymerase (0.1 U per sample) and the set of vectors closed back by blunt-ended ligation (10 U ligase per sample). The average length of the deletion at each time point is determined by restriction analysis of the sets. This yields sets of AK genes deleted from the 5' or the 3' termini. This manipulation is undertaken directly in the pQE-32-Zipper constructs, such that the products can be used directly in activity screening.

Screening for AK activity

As a first step in determining the requirements for fragment complementation, we must determine the minimum N-terminal and C-terminal fragments of AK that, alone, are active. Sets of deletions are individually transformed into E. coli BL21 cells and expression of the AK fragments is induced by IPTG. The sets where a significant number of colonies appear in the presence of G418 serve to indicate the approximate length of N- and C-terminal AK fragments which retain activity. Fragment complementation must therefore be undertaken with fragments taken from within these limits. The zipper-directed fragment complementation is detected as follows: appropriate sets of deletions, or pools of sets, are cotransformed into BL21, expression is induced with IPTG and growth in the presence of varying G418 concentrations is monitored. Large colonies which grow in the presence of high G418 concentrations are selected as giving the most efficiently complementing products.

Directed evolution of optimal AK fragments using "DNA shuffling

After optimal fragments have been selected, the individual fragments are removed by restriction digestion at Sph I and Kpn I allowing for 5' and 3' constant priming regions flanking the N- or C-terminal complementary fragments of AK. These oligonucleotides (2–4 μg) are digested with DNaseI (0.005 units/ul, 100 ul) and fragments of 10–50 nucleotides are extracted from low melting point agarose. PCR is then performed with the fragmented DNA, using Taq polymerase (2.5 units/ul) in a PCR mixture containing 0.2 mM dNTPs, 2.2 mM $MgCl_2$ (or 0 mM for suboptimal PCR), 50 mM KCl, 10 mM Tris.HCl, pH 9.0, 0.1% TritonX-100. A PCR program of 94C/60 sec.; 94C 30 sec.; 55C 30 sec.; 72C 30 sec. times 30 to 50; 72C 5 min. Samples are taken every 5 cycles after 25 cycles to monitor the appearance of reassembled complete fragments on agarose gel. The primeness PCR product is then diluted 1:40 or 1:60 and used as template for PCR with 5', 3' complementary constant region oligos as primers for a further 20 cycles. Final product is restriction digested with Sph I and Kpn I and the products subcloned back into pQE32-Zipper to yield the final library of expression plasmids. As before, E. coli BL21 cells are sequentially transformed with C-terminal or N-terminal complementary fragment-expression vectors at an estimated efficiency of 10⁹ and finally cells cotransformed with the complementary fragment. E. coli are grown on agarose plates containing 1 μg/ ml G418 and after 16 hours the largest colonies are selected and grown in liquid medium at increasing concentrations of G418. Those clones showing the maximal resistance to G418 are then selected and if maximum resistance or greater is reached the evolution is terminated. Otherwise the DNA shuffling proceedure is repeated. Finally, optimal fragments are sequenced and physical properties and enzymatic activity are assessed. This optimized AK PCA is now ready to test for dominant selection in any other cell type including yeast and mammalian cell lines. This strategy can be used to develop any PCA based on enzymes that impart dominant or recessive selection to a drug or toxin or to enzymes that produce a colored or fluorescent product. In the later two cases the end point of the evolution process is at minimum, reatainment of signal for the intact, wild type enzyme or enhancement of the signal. This strategy can also be used in the absense of knowledge of the enzyme structure, whether the enzyme in mono-, di- or multimeric structure. However, knowledge of the enzyme structure does not preclude applying this strategy as well, as described below.

As can be appreciated, knowledge of the enzyme structure can be used to render a more efficient way of using molecular evolution to design a PCA. In this case, the enzyme structure is used to define minimal domains of the protein in question, as was done for DHFR. Instead of generating fragments of completely random length for the N- or C-terminal fragments, we select, during the exonuclease phase, those fragments that at a minimum will code for one of the two domains. For instance, in the case of AK, two well defined domains can be discerned in the structure consisting of residues 1–94 in the N-terminus and residues 95–267 in the C-terminus. Endonuclease digestions are performed as above, but reaction products are selected that will minimally code for one of the two domains. These are then the starting points for fragment selection and evolution cycles as described above.

Heteromeric Enzyme PCA

A further embodiment of the invention relates to PCA based on using heterodimeric or heteromultimeric enzymes in which the entire catalytic machinery is contained within one independently folding subunit and the other subunit provides stability and/or a cofactor to the enzymatic subunit. In this embodiment of PCA, the regulatory subunit is split into complementary fragments and fused to interacting proteins. These fragments are co-transformed/transfected into cells along with the enzyme subunit. As with single enzyme PCA described for DHFR and AK, reconstitution and detection of enzyme activity is dependent on oligomerization domaiN-assisted reassembly of the regulatory subunit reassembly into its native topology. However, the reconstituted subunit then interacts with the intact enzymatic subunit to produce activity. This approach is reminiscent of the USPS system, except it has the advantage that the enzyme in this case is not a constitutive cellular enzyme, but rather an exogenous gene product. As such there is no problem with background activity from the host cell, the enzyme can be expressed at higher levels than a natural gene and can also be modified to be directed to specific subcellular compartments (by subcloning compartment-specific signal peptides onto the N- or C-termini of the enzyme and subunit fragments). The specific advantage of this approach is that while the single enzyme strategy may lead to suboptimal enzymatic activity, in this approach, the enzyme folds independently and may in fact act as a chaperone to the fragmented regulatory subunit, aiding in its refolding. In addition, folding of the fragments may need not be complete in order to impart regulation of the enzyme. This approach is realized by a colorimetric/fluorometric assay we have developed based on the *Streptomyces tyrosinase*. This enzyme catalyzes the conversion of tyrosine to deoxyphenylalanine (DOPA). The reaction can be measured by conversion of fluorocinyl-tyrosine to the DOPA form. The active enzyme consists of two subunits, the catalytic domain (Melc2) and a copper binding domain (Melc1). Melc1 is a small protein of 14 kD that is absolutely required for Melc2 activity. In the assay we are developing, the Melc1 protein is split into two fragments that serve as the complementation part of the PCA. These fragments, fused to oligomerization domains, are coexpressed with Melc2, and the basis of the assay is that Melc2 activity is dependent on complementation of the Melc1 fragments. Stoichiometries of protein complexes can also be addressed (i.e. whether a complex consists of two or three proteins) as follows. One fuses two proteins to the two Melc1 fragments and a third to intact Melc2. It thus can be shown that the minimum complementary active complex of the tyrosinase will require that all three components and therefore a trimer is necessary. A key aspect of this approach is that we can easily demonstrate specific interactions by making one component, specifically the protein-Melc2 fusions catalytic subunit dependent on the other components by underexpressing it in the background of overexpressed Melc1 fragment-protein fusions.

Multimer Disruption-Based PCA

Although applicants have described only fragment complementation of intact proteins, protein domains or subunits as comprising PCA, an alternate enmbodiments relates to PCAs based on the disruption of the interface between, for instance a dimeric enzyme that requires stable association of the subunits for catalytic activity. In such cases, selective or random mutagenesis at the subunit interface would disrupt the interaction and the basis of the assay would be that oligomerization domains fused to the subunits would provide the nessesary binding energy to bring the subunits together into a functional enzyme.

Vector Design in Application to PCAs

The PCA strategies listed thus far have used two-plasmid transformation strategies for expression of complementary fragments. This approach has some advantages, such as using different drug resistance markers to select for optimal incorporation of genes, for instance in transformed or transfected cells or for optimum transformation of complementary plasmids into bacteria and control of expression levels of PCA fragements using different promoters. However, single plasmid strategies have advantages in terms of simplicity of transfection/transformation. Protein expression levels can be controlled in different ways, while drug selection can be achieved in one of two ways: In the case of PCAs based on survival assay using enzymes that are drug resistance markers themselves, such as AK, or where the enzyme complements a metabolic pathway, such as DHFR, no additional drug resistance genes need be incorporated in the expression plasmids. If however the PCA is based on an enzyme that produces a colored or fluorescent product, such as tyrosinase or firefly luciferase, an additional drug resistance gene must be expressed from the plasmid. Expression of PCA complementary fragments and fused cDNA libraries/target genes can be assembled on single plasmids as individual operons under the control of separate inducible or constitutive promoters, or can be expressed polycistronically. In *E. coli* polycistronic expression can be achieved using known interceding region sequences, for instance we use the region in the mel operon from which we derived the tyrosinase melc1-melc2 genes which we have shown to be expressed at high levels in *E. coli* under the control of a strong (tac) promoter. Genes could also be expressed and induced off of independent promoters, such as tac and arabinose. For mammalian expression systems, single plasmid systems can be used for both transient or stable cell line expression and for constitutive or inducible expression. Further, differential control of the expression of one of the complementary fragment fusions, usually the bait-fused fragment, can be controlled to minimize expression. This will be important in reducing background non-specific interactions. Examples of differential control of complementary fragment expression include the following strategies:

i) In polycistronic expression, transient or stable, expression of the second gene will necessarily be less efficient and so this in itself could serve to limit the quantity of one of the complementary fragments. Alternatively, the first gene product can be limited in expression by mutation of an upstream donor/splice site, while the second gene can be put under the control of a retroviral internal initiation site, such as that of ECMV to enhance expression.

ii) Individual complementary fragment-fusion pairs can also be put under the control of inducible promoters, all comercially available including those based on Tet-responsive PhCM*-1 promoter, and/or steroid receptor response elements. In such a system the two complementary fragment genes can be turned on and expression levels controlled by dose dependent expression with the inducer, in these cases tetracycline and steroid hormones.

EXAMPLE 2

Applications of the PCA Strategy to Detect Novel Gene Products in Biochemical Pathways and to Map such Pathways Among the greatest advantage of PCA over other molecular interaction screening methods is that they are designed to be performed both in vivo and in any type of cell. This feature is crucial if the goal of applying a technique is to identify novel interactions from libraries and simultaneously be able to determine if the interactions observed are biologically relevant. The detailed example given below, and other examples at the end of this section illustrate how it is that validation of interactions with PCA is possible. In essence, this is achieved as follows. In biochemical pathways, such as hormone receptor-mediated signaling, a cascade of enzyme-mediated chemical reactions are triggered by some molecular event, such as by hormone binding to its membrane surface receptor. Enzyme interactions with protein substrates and protein-protein or protein-nucleic acid interactions with enzyme-modified substrates then occur. Such biochemical signaling cascades only occur in specific cell types and model cell lines for studying these processes. Therefore, to detect induced interactions, such as with known proteins in a pathway with yet unidentified proteins, one obviously needs to perform such screening in appropriate model cell lines and in the correct cellular compartment. Only the PCA strategy can be used in a general way to do this. Protein-molecular interaction techniques such as yeast two- or three-hybrid techniques cannot be performed in a context where such events occur, except in the limiting case of nuclear interaction in yeast or interactions that are not triggered. There do exist mammalian two-hybrid techniques where it might be possible to detect induced protein interactions, but only again if the proteins involved can be simultaneously activated, transported to the nucleus and interact with their partners. PCAs do not have these limitation since they do not require additional cellular machinery available only in specific compartments. A further point is that by performing the PCA strategy in appropriate model cell types, it is also possible to introduce appropriate positive and negative controls for studying a particular pathway. For instance, for a hormone signaling pathway it is likely that hormone signaling agonists and antagonists or dominant-negative mutants of signaling cascade proteins would be known, that are upstream or act in parallel to the events being examined in the PCA. These reagents could be used to determine if novel interactions detected by the PCA are biologically relevant. In general then, interactions that are detected only if hormone is introduced but are not seen if an antagonist is simultaneously introduced could be hypothesized to represent interactions relevant to the process under study.

Below is a detailed description of an application of the DHFR that illustrates these points, as well as further examples where the PCA strategy could be used.

Application of the DHFR PCA to Mapping Growth Factor-Mediated Signal Transduction Pathways One of the earliest detectable events in growth factor-activated cell proliferation is the serine phosphorylation of the S6 protein of the 40S ribosomal subunit. The discovery of serine/threonine kinases that specifically phosphorylate S6 have considerably aided in identifying novel mitogen mediated signal transduction pathways. The serine/threonine kinase p70S6k has been identified as a specific S6 phosphorylase[131-136]. p70S6k is activated by serine and threonine phosphorylation at specific sites in response to several mitogenic signals including serum in serum starved cells, growth factors including insulin and PDGF, and by mitogens such as phorbol esters. Considerable effort has been made over the last five years to determine how p70/p85S6k are activated in response to mitogens. Two receptor-mediated pathways have been implicated in p70S6k activation, one associated with the phosphatidylinositol-3-kinase (PI(3)k) and the other with the PI(3)k homologue mTOR[137-144]. Key to understanding of this proposal, is the fact that the role of these enzymes in activation of p70S6k was determined by effects of two natural products on phosphorylation and enzyme activity: rapamycin, which indirectly inhibits mTOR activity, and wortmannin, which directly inhibits PI(3)k activity. It is also important to note that no direct upstream kinases or other regulatory proteins of p70S6k have been identified to this date.

The interactions of p70S6k with its known substrate S6 can be studied as a test system for the DHFR PCA in *E. coli* and in mammalian cell lines. One can also seek to identify novel interactions with this enzyme that would lead to new insights into how this important enzyme is regulated. Also, since activation of the enzyme is mediated by multiple pathways that can be selectively inhibited with specific drugs, this is an ideal system to test PCAs as methods to distinguish induced versus constitutive protein-protein interactions.

a) Testing of the *E. coli* survival assay: Interaction of p70S6k with S6

This test is ideal, because the apparent Km (=250 nM) of p70S6k for S6 protein[145] is approximately the same as the Kd for leucine zipper-forming peptides from GCN4 used in our test system. However, we will have to use a constitutively active form of the enzyme for our tests. An N-terminal truncated form of the enzyme D77-p70S6k, is constitutively active and will be used in these studies147.

Methodology: D77-p70S6k-F[1,2] fusion and D77-p70S6k-F[3] fusion, or F[1,2] and D77-p70S6k-F[3] fusion (as a control) will be cotransformed into *E. coli* and the cells grown in minimal medium in the presence of trimethoprim. Colonies will be selected and expanded for analysis of kinase activity against 40S ribosomal subunits, and for coexpression of the two proteins.

b) Modification of the bacterial survival assay for library screening: Identification of Novel Interacting Proteins.

Screening an expression library for interactions with a given target (p70S6k-D77, in this case) will be straightforward in this system, given that the only steps involved are: 1-construction of the fusion-expression library as a fusion with mDHFR fragment[3]; 2-transformation of the library in *E. coli* BL21 harboring pRep4 (for constitutive expression of the lac repressor; this is required in the case where a protein product is toxic to the cells) and a plasmid coding for the fusion: p70S6k-D77-[1,2]; 3-plating on minimal medium in the presence of trimethoprim and IPTG; 4-selection of any colonies that grow, propagation and isolation of plasmid DNA, followed by sequencing of DNA inserts; 5-purification of unknown fusion products via the hexaHis-tag and sizing on SDS-PAGE.

Methodology:

The overall strategy is illustrated in FIG. 5. 1-Construction of a directional fusioN-expression library: i-cDNA production: One can isolate poly(A)+ RNA from BA/F3 cells (B-lymphoid cells) because these cells have successfully been used in the study of the rapamycin-sensitive p70S6k activation cascade[139]. To enrich for full-length mRNA, we will affinity purify the mRNA via the 5' cap structure by the CAPture method[148]. Reverse transcription will be primed by a "Linker Primer": it has a poly(T) tail to prime from the poly(A) mRNA tail, and an XhoI site for later use in directional subcloning of the fragments. The first strand is then methylated. After second strand synthesis and blunting of the products, "EcoRI Adapters" are added, producing digestion of the linkers with EcoRI and XhoI (the inserts are protected by methylation) produces full-length cDNA ready for directional insertion in a vector opened with EcoRI and XhoI. Because the success of library screening depends largely on the quality of the cDNA produced, we will use the above methods as they have proven to consistently produce high-quality cDNA libraries. ii-Insertion of the cDNA into vectors: The library will be constructed as a C-terminal fusion to mDHFR F[3] in vector pQE-32 (Qiagen), as we have obtained high levels of expression of mDHFR fusions from this vector in BL21 cells. Three such vectors will be created, differing at their 3' end, which is the novel polycloning site that we engineered (described earlier, under Methods), carrying either 0, 1, or 2 additional nucleotides. This allows read-through from F[3] into the library fragments in all 3 translational reading frames. The cDNA fragments will be directionally inserted at the EcoRI and XhoI sites in all three vectors at once. 2, 3, 4, and 5- These steps have been described earlier, under Results, apart from the final sequencing of clones identified using sequencing primers specific to vector sequences flanking sites of library insertion. The protein purification will also be as described earlier, by a one-step purification on Ni-NTA (Qiagen). If the product size is more than 15 kDa over the molecular weight of the DHFR component (equal to a cDNA insert of more than 450bp), we will have the inserts sequenced at the Sheldon Biotechnology Center (McGill University).

c) Development of the Eukaryotic Assay

The transformation of the system described above, is useful to produce an equivalent assay for use in eukaryotic cells. The basic principle of the assay is the same: the fragments of mDHFR are fused to associating domains, and domain association is detected by reconstitution of DHFR activity in eukaryotic cells (FIG. 5).

Creation of the expression constructs: The DNA fragments coding for the GCN4-zipper-mDHFR fragment fusions were inserted as one piece into pMT3, a eukaryotic transient expression vector[126]. Expression of the fusion proteins in COS cells was apparent on SDS-PAGE after 35[S]Met labeling.

Survival assays in eukaryotic cells: Two systems can be used for detection of mDHFR reassembly, in parallel: i- CHO- DUKX B11 cells (Chinese Hamster Ovary cell line deficient in DHFR activity) are cotransfected with GCN4-zipper-mDHFR fragment fusions. The cells are grown in the absence of nucleotides; only cells carrying reconstituted DHFR will undergo normal cell division and colony formation. ii-Methotrexate (MTX)-resistant mutants of mDHFR have been created, with the goal of transfecting cells that have constitutive DHFR activity such as COS and 293 cells. We mutated F[1,2] in order to incorporate, one at a time, each of five mutations that significantly increase Ki (MTX): Gly15Trp, Leu22Phe, Leu22Arg, Phe31Ser and Phe34Ser (numbering according to the wild-type mDHFR sequence). These mutations occur at varying positions relative to the active site and relative to F[3], and have varying effects on Km (DHF), Km (NADPH) and Vmax of the full-length mammalian enzymes in which they were. Mutants Z-F[1,2: Leu22Phe], Z-F[1,2: Leu22Arg] and Z-F[1,2: Phe31Ser] all allowed for bacterial survival with high growth rates when cotransformed with Z-F[3] (results not shown).The five mutants will be tested in eukaryotic cells, in reconstitution of mDHFR fragments to produce enzyme that can sustain COS or 293 cell growth while under the selective pressure of MTX, which will eliminate background due to activity of the native enzyme. The mutations offers an advantage in selection while presenting no apparent disadvantage with respect to reassembly of active enzyme. If the reconstituted mDHFR produced in either of the survival assays allows eukaryotic cell growth that is significantly slower than growth with the wild-type enzyme, thymidylate will be added to the growth medium to partially relieve the selective pressure offered by the lack of nucleotides.

d) Testing of the eukaryotic survival assay

It is necessary at the outset to test whether induced interactions with p70S6k can be detected. One can use the same test system as that for the *E. coli* test system described above: Induction of association of p70S6k with S6 protein.
Methodology:
mDHFR Leu22Phe mutant S6-F[1,2] and p70S6k-F[3], or F[1,2] and p7control) will be cotransfected into COS cells and the cells will be serum starved for 48 hours followed by replating of cells at low density in serum and MTX. Colonies will be selected and expanded for analysis of kinase activity against 40S ribosomal subunits, and for coexpression of the two proteins. Further controls will be performed for inhibition of protein association with wortmannin and rapamycin.

e) Modification of the eukaryotic survival assay for library screening

An important part of the work required in creating a library for use in eukaryotic cells will have been accomplished already, as the EcoRI/Xhol directional cDNA produced by the Stratagene "cDNA Synthesis Kit" can directly be inserted directionally into the Stratagene Zap Express vector.
Methodology:
Steps 1 through 5 are parallel to those for the bacterial library screening (above). 1-Again, the library is constructed as a C-terminal fusion to mDHFR F[3]. F[3] (with no stop codon) will be inserted in frame in Zap Express, followed by insertion of the novel polylinkers allowing expression of the inserts in all three reading frames (described above), and by the EcoRI/Xhol directional cDNA. This bacteriophage library will be propagated and treated with the Stratagene helper phage to excise a eukaryotic expression phagemid vector (pBK-CMV) carrying the fusion inserts. 2-Cotransfection of the library and p70S6k-F[1,2] constructs in eukaryotic cells: we will perform the screening in COS or 293 cells, as these are responsive to serum in activating the p70S6k signaling pathway. Selection experiments will be performed as described for the S6 test system above. 3-Propagation, isolation and sequencing of the insert DNA will be undertaken. 4-The cloned fusion proteins will be sized on SDS-PAGE by direct visualization after 35S-Met/Cys labeling, or by Western blotting using a commercial polyclonal antibody to mDHFR.

Generalization of the Strategy: The scheme for detecting partners for the protein p70S6k can be applied to studies of any biochemical pathway in any living organism. Such pathways may also be related to disease processes. The disease-related pathway may be an intrinsic process of cells in humans where a pathology arises from, for instance mutation, deletion or under or over expression of a gene. Alternatively the biochemical pathway may be one that is specific to a pathogenic organism or the mechanism of host invasion. In this case, component proteins of such processes may be targets of a therapeutic strategy, such as development of drugs that inhibit invasion by the organism or a component enzyme in a biochemical pathway specific to the pathogenic organism.

Inflamatory diseases are a case in point that can concern both examples. The protein-protein interactions that mediate the adhesion of leukocytes to inflamed tissues are known to involve such proteins as vascular cell adhesion molecule-1 (VCAM-1), and certain cytokines such as IL-6 and IL-8 that are produced during inflammation. However, many of the proteins involved in onset of inflammatory response remain unknown; further, the intracellular signaling pathways triggered by the extracellular associations are poorly understood. The PCAs could be used in elucidation of the mechanisms underlying the onset of inflammation, as well the ensuing signaling. For example, signaling pathways associated with inflamation, such as those mediated by IL-1, IL-6, IL-8 and tumor necrosis have been studied in some detail and many direct and downstream regulators are known. These regulators can be used as starting point targets in a PCA screening to identify other signalling or modulating proteins that could also be targets for drug development.

There is an increased risk of infection by enteric pathogens in the occurrence of the intestinal inflammation that characterizes idiopathic intestinal diseases. There are two mechanisms which need to be better understood here and which can be addressed by PCA:

i-the cellular mechanisms of inflammation as described above, and ii-the discovery of the specific cell-surface ligands which the pathogenic organisms recognize and associate with. Secreted proteins produced by the pathogen can bind to the basolateral membrane of epithelial cells (as in the case in *Yersinia pseudotuberculosis* infection) or be translocated into intestinal epithelial cells (Salmonella infection), promoting infectivity and/or physiological responses to the infection. However, in most cases the interactions between the pathogenic protein and the epithelial cells are unknown.

Cell adhesion and nervous system regeneration

A related example in cell adhesion includes processes involved in develoment and regeneration in the nervous system. Cadherens are membrane proteins that mediates calcium dependent cell-cell adhesion. To do so they need another class of cytoplasmic proteins called cathenins. Those make a bridge between cadherins and cytoskeleton. Cathenins are also regulate genes that control differentiation-specific genes. For instance, the protein B-cathenin can interact in certain situation with a transcription factor (lef-1) and be translocated into the nucleus where it constrains the number of genes transactivated by lef-1 (differentiation). This process is regulated by the Wnt signaling pathway (homologs to the wingless pathway in drosophila) by inactivation of GSK3B which permit degradation after of APC (a cytoplasmic adapter protein). PCA strategies could be used to identify novel proteins involved in the regulation of these processes.

Proteins involved in viral integration processes are examples of targets that could be tested for inhibitors using the PCA strategies. Examples for the HIV virus include:
i) inhibition of integrase or the transport of the pre-integration complex: protein Ma or vpr.
ii) Inhibition of the cell cycle in G2 by vpr (interaction by cyclin B) causing induction of apoptosis.
iii) Inhibition of the interaction of gp160 (precursor of the membrane proteins) with furine.

Accessory proteins of HIV as a therapeutic target:
i) Vpr: nuclear localizing sequence (target): interaction site of vpr with phosphatasesA.
ii) vif: interaction with vimentin (cytoskeleton associated protein).
ii) Vpu: Degradation of CD4 in the RE mediated by the cytoplasmic tail of Vpu.
iii) nef: Myristoylation signal of Nef.

EXAMPLE 3

Other Examples of Protein Fragment Complementation Assays

Other examples of assays are herein examplified. The reason to produce these assays is to provide alternative PCA strategies that would be appropriate for specific protein association problems such as studying equilibrium or kinetic aspects of assembly. Also, it is possible that in certain contexts (for example, specific cell types) or for certain applications, a specific PCA will not work but an alternative one will. Further below are brief descriptions of each other PCAs embodiments.

1) Glutathione-S-Transferase (GST) GST from the flat worm *Schistosoma japonicum* is a small (28 kD), monomeric, soluble protein that can be expressed in both prokaryotic and eukaryotic cells. A high resolution crystal structure has been solved and serves as a starting point for design of a PCA. A simple and inexpensive calorimetric assay for GST activity has been developed consisting of the reductive conjugation of reduced glutathione with 1-chloro-2,4-dinitrobenzine (CNDB), a brilliant yellow product. We have designed a PCA based on similar structural criteria used to develop the DHFR PCA using GCN4 leucine zippers as oligomerization domains. Cotransformants of zipper-GST-fragment fusions are expressed in *E. coli* on agar plates and colonies are transferred to nitrocellulose paper. Detection of fragment complementation is detected in an assay where a glutathione-CDNB reaction mixture is applied as an aerosol on the nitrocellulose and colonies expressing co-expressed fragments of GST are detected as yellow images.

2) Green Fluorescent Protein (GFP) GFP from Aequorea Victoria is becoming one of the most popular protein markers for gene expression. This is because the small, monomeric 238 amino-acids protein is intrinsically fluorescent due to the presence of an internal chromophore that results from the autocatalytic cyclization of the polypeptide backbone between residues Ser65 and Gly67 and oxidation of the − bond of Tyr66. The GFP chromophore absorbs light optimally at 395 nm and possesses also a second absorption maximum at 470 nm. This bi-specific absorption suggests the existence of two low energy conformers of the chromophore whose relative population depends on local environment of the chromophore. A mutant Ser65Thr that eliminates isomerization (single absorption maximum at 488 nm) results in a 4 to 6 times more intense fluorescence than the wild type. Recently the structure of GFP has been solved by two groups, making it now a candidate for a strucutre-based PCA-design, which we have begun to develop. As with the GST assay, we are doing all of our initial development in *E. coli* with GCN4 leucine zipper-forming sequences as oligomerization domains. Direct detection of fluorescence by visual observation under broad spectrum UV light will be used. We will also test this system in COS cells, selecting for co-transfectants using fluorescence activated cell sorting (FACS).

3) Fire Fly Luciferase. Firefly luciferase is a 62 kDa protein which catalyzes oxidation of the heterocycle luciferin. The product posesses one of the highest quantum yields for bioluminescent reactions: one photon is emitted for every oxidized luciferin molecule. The structure of luciferase has recently been solved, allowing for strucutre-based development of a PCA. As with our GST assay, cells are grown on a nitrocellulose matrix. The addition of the luciferin at the surface of the nitrocellulose permits it to diffuse across the cytoplasmic membranes and trigger the photoluminescent reaction. The detection is done immediately on a photographic film. Luciferase is an ideal candidate for a PCA: the detection assays are rapid, inexpensive, very sensitive, and utilizes non-radioactive substrate that is available commercially. The substrate of luciferase, luciferin, can diffuse across the cytoplasmic membrane (under acidic pH), allowing the detection of luciferase in intact cells. This enzyme is currently utilized as a reporter gene in a variety of expression systems. The expression of this protein has been well characterized in bacterial, mammalian, and in plant cells, suggesting that it would provide a versatile PCA.

4) Xanthine-guanine phosphoribosyl transferase (XGPRT) The *E. coli* enzyme XGPRT converts xanthine to xanthine monophosphate (XMP), a precursor of GMP. Because the mammalian enzyme hypoxanthine-guanine phosphoribosyl transferase HGPRT can only use hypoxanthine and guanine as substrates, the bacterial XGPRT can be used as a dominant selection assay for a PCA for cells grown in the presense of xanthine. Vectors expressing XGPRT confer the ability of mammalian cells to grow in selective medium containing adenine, xanthine, and mycophenolic acid. The function of mycophenolic acid is to inhibit de novo synthesis of GMP by blocking the conversion of IMP into XMP (Chapman A. B., (1983) Molec. & Cellul. Biol. 3, 1421–1429). The only GMP produced then come from the conversion of xanthine into XMP, catalyzed by the bacterial XGPRT. As with aminoglycoside phosphotransferase fragments of XGPRT can be generated based on the known structure (See table 1.) using the design-evolution strategy described above with fragments fused to the GCN4 leucine zippers as a test oligomerization domains. The complementary fusions are cotransfected and the proteins transiently expressed in COS-7 cells, or stability expressed in CHO cells, grown in the selective medium. In the case of CHO cells, colonies are collected and sequentially re-cultured at increasing concentrations of the selective compounds in order to enrich for populations of cells that efficiently express the fusions at high concentrations.

5) Adenosine deaminase Adenosine deaminase (ADA) is present in minute quantities in virtually all mammalian cell. Although it is not an essential enzyme for cell growth, ADA can be used in a dominant selection assay. It is possible to establish growth conditions in which the cells require ADA to survive. ADA catalyzes the irreversible conversion of cytotoxic adenine nucleosides to their respective nontoxic inosine analogues. By adding cytotoxic concentrations of adenosine or cytotoxic adenosine analogues such as 9-b-D-xylofuranosyladenine to the cells, ADA is required for cell growth to detoxify the cytotoxic agent. Cells that incorporate the ADA gene can then be selected for amplification in the presence of low concentrations of 2'-deoxycoformycin, a tight-binding transition state analogue inhibitor of ADA. ADA can then be used for a PCA based on cell survival (Kaufman, R. J. et al. (1986) Proc. of the Nat. Acad. Sci. (USA) 83, 3136–3140). As with the other systems described above, fragments of ADA can be generated based on the known structure (See table 1.) using the design-evolution strategy described above with fragments fused to the GCN4 leucine zippers as a test oligomerization domains. The complementary fusions are cotransfected and the proteins transiently expressed in COS-7 cells, or stability expressed in CHO cells, grown in the selective medium containing 2'-deoxycoformycin. In the case of CHO cells, colonies are collected and sequentially re-cultured at increasing concentrations of 2'-deoxycoformycin in order to enrich for populations of cells that efficiently express the fusions at high concentrations 6) Bleomycin binding protein (zeocin resistance gene) Zeocin, a member of the leomycin/phleomycin family of antibiotics, is toxic to bacteria, fungi, plants, and nammalian cells. The expression of the zeocin resistance gene confers resistance to bleomycin/zeocin. The protein confers resistance by binding to and sequestering the drug and thus preventing its association and hydrolysis of DNA. Berdy, J. (1980) In *Amino Acid and Peptide Antibiotics*, J. Berdy, ed. (Boca Raton, FL: CRC Press), pp.459–497; Mulsant, P., Tiraby, G., Kallerhoff, J., and Perret, J. (1989 Somat. Cell. Mol. Genet. 14, 243–252). Bleomycin binding protein (BBP) could then be used for a PCA based on cell survival. As with the other systems described above, fragments of ADA can be generated based on the known structure (See table 1.) using the design-evolution strategy described above with fragments fused to the GCN4 leucine zippers as a test oligomerization domains. The BBP is a small (8 kD) dimer that binds to drugs via a subunit interface binding site. For this reason, the design would be somewhat different in that first, a single chain form of the dimer would be generated by making a fusion of two BBP genes with a short sequence coding for a simple polypeptide linker introduced between the two subunits. Fragments in this case will be based on a short sequence of one of the subunit modules, while the other fragment will be composed of the remaining sequence of the subunit plus the other subunit. Complementation and selection experiments will be performed as described for the examples above using bleomycin or zeocin as selective drugs.

7) Hygromycin-B-phosphotransferase. The antibiotic hygromycin-B is an aminocyclitol that inhibits protein synthesis by disrupting translocation and promoting misreading. The *E. coli* enzyme hygromycin-B-phosphotransferase detoxifies the cells by phosphorylating Hygromycin-B. When expressed in mammalian cells, hygromycin-B-phosphotransferase can confer resistance to hygromycin-B (Gritz, L., and Davies, J. (1983) Gene 25, 179–188.). The enzyme is a dominant selectable marker and could be used for a PCA based on cell survival. While the structure of the enzyme is not known it is suspected that this enzyme is homologous to aminoglycoside kinase (Shaw, et al. (1993) Microbiol. Rev. 57, 138–163). It is therefore possible to use the combined design/evolution strategy to produce a PCA with this enzyme and perform dominant selection in mammalian cells with selection at increasing concentrations of hygromycin 8) L-histidinol AND+oxydoreductase. The hisD gene of *Salomonella typhimurium* odes for the L-histidinol AND+ oxydoreductase that converts histidinol to histidine. Mammalian cells grown in media lacking histidine but containing histidinol can be selected for expression of hisD (Hartman, S. C., R. C. Mulligan (1988) Proc. of the Nat. Acad. Sci. (USA) 85, 8047–8051). An additional advantage of using hisD in dominant selection is that histidinol is itself toxic, inhibiting the activity of endogenous histidyl-tRNA synthetase. Histidinol is also inexpensive and readily permeates cells. The structure of histidinol NAD+oxydoreductase is unknown and so development of a PCA based on this enzyme is based entirely on the exonuclease fragment/evolution strategy. The following Table list alternative embodiments using other PCA reporters. Abrevations in Table: Type: D, dominant selection marker; R, recessive selection marker. Structure: four letter codes=Protein Data Bank (PDB) entries; K, known but not deposited in PDB; U, unknown. mono/oligo: M, monomer; D, dimer; tetra, tetramer.

TABLE 1

A list of Other Potential PCA Reporter Candidates

| Enzyme | Type | Structure | Size | Mono/Oligo | Selection drugs/Conditions |
|---|---|---|---|---|---|
| A-Assays based on Dominant or Recessive Selection | | | | | |
| DHFR | R/D | many | 18 kD | M | methotrexate/trimethoprim |
| Adenosine deaminase | D/R | 1ADD | | M | Xyl-A or adenosine, alanosine, and 2'-deoxycoformycin |
| Thymidine kinase | D/R | 1KIN | | D | gangcyclovene, HAT |
| Mutant hypoxanthine- guanine phosphoribosyl transferase | D | 1HGM | | D | HAT + thymidine kinase |
| Thymidylate synthetase | R | 1NJE | 35 kd | M | 2 fluorodeoxyuridine |
| Xanthine-guanine phosphoribosyl transferase | D | 1NUL | | | mycophenolic acid with limiting xanthine |
| Glutamine synthetase | R | 2LGS | | | |
| Asparagine synthetase | R | U | | | B-aspartyl hydroxamate or albizin |
| Puromycin N-acetyltransferase | D | U | 23 kD | M | puromycin |
| Aminoglycoside phosphotransferase | D | K | 35 kD | M | neomycin, G418, gentamycin |
| Hygromycin B phosphotransferase | D | U | | M | hygromycin B |
| L-histidinol: NAD + oxidoreductase | D | U | 46 kD | M | histidinol |
| Bleomycin binding protein | D | K | 8 kD | D | bleomycin/zeocin |
| Cytosine methyltransferase | R/D | U | | | 5-Azacytidine (5-aza-CR) and 5-aza-2'-deoxycytidine |
| O6-alkylguanine alkyltransferase | D | 1ADN | | | N-methyl-N-nitrosourea |
| Glycinamide ribonucleotide transformylase | R | 1GRC | 23.2 kD | D | dideazatetrahydrofolate, minus purine |

TABLE 1-continued

A list of Other Potential PCA Reporter Candidates

| Enzyme | Type | Structure | Size | Mono/Oligo | Selection drugs/Conditions |
|---|---|---|---|---|---|
| Glycinamide ribonucleotide synthetase | R | U | 45.9 kD | | minus purine |
| Phosphoribosyl-aminoimidazole synthetase | R | U | 36.7 kD | | minus purine |
| Formylglycin-amide ribotide amidotransferase | R | U | 141.4 kD | M | L-azaserine, 6-diazo-5-oxo-L-nor-leucine, minus purine |
| Phosphoribosyl-aminoimidazole carboxylase | R | U | 39.5 kD | D | minus purine |
| Phosphoribosyl-aminoimidazole carboxamide for-myltransferase | R | U | 57.3 kD | | minus purine |
| Fatty acid synthase | R | | 272 kD | D | cerulenin |
| IMP dehydrogenase | R | 1AK5 | 55.4 kD | Tetra | mycophenolic acid |
| *ii-Viral Plaque Assays* | | | | | |
| Thioredoxin | D | 1TDF | 34.5 kD | D | |
| Reverse transcriptase | D | 3HVT | | | |
| Viral protease | D | | | | |
| *B-Cell Death Assays* | | | | | |
| Cysteine protease: papain | D | 1STF | 38.9 kD | M | inhibited by cystatin |
| Cysteine protease: caspase | D | 1CP3 | 17 kd + 12 kD | Hete-roD | inhibited by DEVD-aldehyde (can also by used in a fluori-metric or colorime-tric assay, in vitro) |
| Metalloprotease: carboxypeptidase | D | | 47.1 kD | M | inhibited by methyl-ethyl succinic acid |
| Serine protease: proteinase K | D | 1PTK | 30.6 kD | M | inhibited by serpins |
| Aspartic protease: pepsin | D | 1PSN | 34.5 kD | M | inhibited by pep-statin A (can also be used in an fluorime-tric assay, in vitro) |
| Lysozyme | D | many | 23.2 kD | M | inhibited by N-ace-tylglucosamine trisaccharide |
| RNAse | D | many | 13.3 kD | M | inhibited by RNAse inhibitor |
| DNAse | D | 1DNK | 61.6 kD | M | inhibited by actin |
| Phospholipase A2 | D | 1P2P | 13.8 kD | M/D | many inhibitors: bromophenacyl bromide, hexadecyl-trifluoroethyl-gly-cerophosphometha-nol, bromoenol lac-tone, etc. |
| Phospholipase C | D | 1AH7 | 28 kD | M | many inhibitors: neomycin, chelery-thrine, U73122, etc. |
| *C-Colorimetric/Fluorimetric Assay* | | | | | |
| DT-Diaphorase (NAD(P)H-[qui-none acceptor] oxidoreductase) | | 1QRD | 26 kD | D | NADPH-diaphorase stain, inhibited by dicumarol, Cibacron blue and phenidione Note: can also be used in a cell death assay (+nitrobenzi-midazole, fo example). |
| (NAD(P)H-[qui-none acceptor] oxidoreductase)-2 | | isoform of 1QRD | 21 kD | D | NRH-diaphorase stain, inhibited by pentahydroxyfla-vone |
| Thermophilic dia-phorase (*Bacillus stearothermophilus*) | | | 30 kD | M | NADH-diaphorase stain |
| Glutathione-S-transferase | | 1GNE | 26 kD other iso-form of 28 kD | D | production of a yel-low product by the conjugation of glu-tathione with an aro-matic substance, chloro dinitroben-zene (CDNB) |
| Luciferase | | 1LCI | 62 kD | M | Fluorometric |
| Green-fluore-scent protein | | 1EMA | 30 kD | M | Intrinsic fluores-cence |
| Chloramphenicol acetyltransferase | | 1CLA | 25 kD | Tri | Fluorimetric: Bod-ipy chloramphenicol |
| Uricase | | | 32 kD | Tetra | Fluorometric |
| SEAP (secreted form of human placental alkaline phosphatase) | | 1AJA | | M | CSPD chemilumine-scent substrate |
| B-Glucuronidase | | 1BHG | 71 | Tetra | Histochemical, flu-orometric or spec-trophotometric assays using various substrates such as X-GLUC. |
| *D-Heteromeric Enzyme Strategies* | | | | | |
| Tyrosinase | | | 30 kD + 14 kD | Hetero M + M | Colorimetric: synthesis of melanin |

EXAMPLE 4

Examples of Variants of PCA to Detect Multiple Protein/protein-dna/protein RNA/protein-drug Complexes To this point specific examples have only been made of applications of PCA to protein-pair interactions. However, it is possible to apply PCA to multiprotein, protein-RNA, protein-DNA or protein-small molecule interactions. There are two general schemes for achieving such systems. Multi-subunit PCA: Two proteins need not interact for a PCA signal to be observed; if a partner protein or protein complex binds to two proteins simultaneously, it is possible to detect such a three protein complex. A multusubunit PCA is conceived with the example of herpes simplex virus thymi-dine kinase (TK), a homodimer of 40 kD. In this conception, the TK structure contains two well defined domains con-sisting of an alpha/beta (residues 1-223) and an alpha-helical domain (224–374). As a test system, we use the Rop1 dimer, a four helix bundle homodimer. The two fragments of TK are extracted by PCR and subcloned into the transient transfection vector pMT3, the first in tandem to the Adeno-visus major late promoter, tripartite leader 3' to the first ATG, and the second downstream of a ECMV internal initiation site. Restriction sites previously introduced between the first and the last ATG are subcloned into BamHI/Kpnl and Pstl/EcoRI cloning sites downstream of the two ATGs.

These are used to subclone PCR-generated fragments of the Rop1 subunits into two different vectors. Subsequently Ltk-cells are cotransfected by lipofection with the two plasmids and colonies of surviving cells are serially selected in medium containing increasing concentrations of HAT (hypoxanthine/aminopterin/thymidine). Cells that express complementary fragments of TK fused to the four Rop1 will proliferate under this selective pressure, or otherwise die. Specific examples of use of this concept would be in determining constituents of multiprotein complexes that are formed transiently or constitutively in cells.

The utility of PCA is not limited to detecting protein-protein interactions, but can be adapted to detecting interactions of proteins with DNA, RNA, or small molecules. In this conception, two proteins are fused to PCA complementary fragments, but the two proteins do not interact with each other. The interaction must be triggered by a third entity, which can be any molecule that will simultaneously bind to the two proteins or induce an interaction between the two proteins by causing a conformational change in one or both of the partners. Two examples have been demonstrated in our lab using the mDHFR PCA in E. coli. In the first case a natural product, the immunosuppressant drug rapamycin, is used to induce an interaction between its receptor FKBP12 and a partner protein mTOR (mammalian Target of Rapamycin). We detect this by cotransformation of DHFR fragments fused to FKBP or mTOR into E. coli grown in the presence or absence of trimethoprim (as described above) and rapamycin (0–10 nM). We have demonstrated that support of growth as detected by colony formation is completely dependent on the addition of rapamycin, suggesting that the mDHFR PCA is detecting a rapamycin-induced assembly of a FKBP12-mTOR and subsequent reconstitution of DHFR activity. This is one example of a use of the PCA strategy to test for small molecules that can induce interactions between proteins. General applications could be made to therapeutic development, in the form screening small molecule combinatorial compound libraries for molecules that induce interactions between proteins, that may inhibit the activities of either or both of the proteins, or activate specific cellular processes that are initiated by other events, such as growth factor-mediated receptor dimerization. The discovery of such small molecules could lead to the development of orally available drugs for the treatment of a broad spectrum of human diseases.

Another example of an induced interaction we have studied with the DHFR PCA is the interaction of the oncogene GTPase p21 ras and its direct downstream target, the serine/threonine kinase raf. This interaction only occurs when the GTPase is in the GTP-bound form, whereas turnover of GTP to GDP leads to release of the complex. As with the FKBP-mTOR complex, we have demonstrated this induced interaction in E. coli. PCA could be used in a general way to study such induced interactions, and to screen for compounds that release or prevent these interactions in pathological states. The ras-raf interaction itself could be a target of therapeutic intervention. Oncogenic forms of ras consist of mutants that are incapable of turning over GTP and therefore remain continuously associated with activated ras. This leads to a constitutive uncontrolled growth signal that results, in part, in oncogenesis. The identification of compounds that inhibit this process, by PCA, would be of value in broad treatment of cancers. Other examples of multimolecular applications of PCA could include identification of novel DNA or RNA binding proteins. In its simplest conception one uses a known DNA or RNA binding motifs, for instance a retinoic acid receptor zinc finger, or a simple RNA binding protein such as IF-1, respectively. One half of the PCA consists of the DNA or RNA protein binding domain fused to one of the PCA fragments (control fragment). The complementary fragment is fused to a cDNA library. A third entity, the gene coding for a sequence containing an element known to bind to the control protein, and then a second putative or known regulatory element is coded for after this sequence. A test system consists of tat/tar elements that control elongation in transcription/translation of HIV genes. An example application would be identification of tat binding elements that have been proposed to exist in eukaryotic genomes and may regulate genes in the same or similar way to that of HIV genes. (SenGupta D. J. et al. (1996) Proc. Natl. Acad. USA 6, 8496–8501).

EXAMPLE 5

Examples of PCA Applications to Drug Screening: Screening Combinatorial Libraries of Compounds for Those that Inhibit or Induce Protein-protein/ protein-rna/protein-DNA Complexes A) Drug screening.

Screening combinatorial libraries of compounds for those that inhibit or induce protein-protein/protein-rna/protein-DNA complexes. The PCA strategy can be directly applied to identifying potentially therapeutic molecules contained in combinatorial libraries of organic molecules. It is possible to perform high throughput screening of such libraries to screen for compounds that will inhibit or induce protein-protein interactions or protein-DNA/RNA interactions (as discussed above). In addition it is also possible to screen for compounds that inhibit enzymes whose substrates are other proteins DNA, RNA or carbohydrates, as discussed below. In this application, proteins that interact/protein substrate pairs, or control DNA/RNA binding protein-enzyme pairs are fused to PCA complementary fragments and plasmids harboring these pairs are transformed/transfected into a cell, along with any third DNA or RNA element as the case requires. Transformed/transacted cells are grown liquid culture in multiwell plates where each well is inoculated with a single compound from an array of combinatorially synthesized compounds. A readout of a response depends on the effect of a compound. If the compound inhibits a protein interaction, there is a negative response (no PCA signal is the positive response). If the compound induces a protein interaction, the response is a positive PCA signal. Controls for non-specific effects of compounds include: 1) demonstration that the compound does not effect the PCA enzyme itself (test against cells transfected with the wild-type intact enzyme used as the PCA probe) and in the case of a cell survival assay, that the compound is not toxic to the cells that have not been transformed/transfected. As well as providing a high throughput assay for biological activity of compounds, PCA also offers the advantage over in vitro assays that it is a test for cell membrane permeability of active compounds. Specific demonstrated examples of PCA for drug screening in our laboratory include the application of DHFR PCA in E. coli to detecting compounds that inhibit therapeutically relevant targets. These include Bax/Bcl2 fkbp12/tor ras/raf, carboxyl terminal dimerization domain of HIV-1 capsid protein, IkB kinase IKK-1 and IKK-2 dimerization domains (leucine zippers and helix-loop-helix domains). In each case, the two proteins are subcloned 5' upstream of either F[1,2] or F[3] as described above. Plasmids harboring the complementary fragments are cotransformed into BL21 cells. Colonies from minimal medium plates containing IPTG and trimethoprim are picked, and grown in liquid medium under the same selective conditions and frozen stocks made. For a single screening cycle, a priming overnight culture is grown from frozen stocks in LB medium. A selective minimal medium containing trimethoprim, ampicillin, IPTG is aliquated at 25 ml into each well of a 384 well plate. Each well is then inoculated with 1 ul of an individual sample from a compound array (ArQule Inc.) to give a final concentration of 10 uM. Each well is then inoculated with 2 ml of overnight culture and plates are incubated in a specially adapted shaker bath at 37C. At 2 hour intervals, plates are read on an optical absorption spectroscopic plate reader coupled to a PC and spreadsheet software at 600 nm (scattering) for a period of 8 hours. Rates of growth are calculated from individual time readings for each well and compared to a standard curve. A "hit" is defined as a case where an individual compound reduces the rate of growth to less than the 95% confidence interval based on the standard deviation for growth rates observed in all of the wells within the test plate. "Near hits" are defined as those cases where growth rates are within the 95% confidence interval. For each of the hits or near hits, the following controls are then performed: The same experiment is performed with BL21 cells that are transformed with empty vector (and no trimethoprim), with vector harboring the full length mDHFR gene, or with cotransfected cells where protein expression is not induced by IPTG. If in all of these cases the compound has no effect, it can be concluded that it is specifically disrupting the protein-protein interaction being tested. Such validated hits or near hits are then retested to establish a dose-response curve for the individual compound, with concentrations varying from 1 pM up to 1 $\mu$M by orders of magnitude of 10. The PCA strategy for compound screening can also be applied in the multiprotein protein-RNA/DNA cases as described above, and can easily be adapted to the DHFR or any other PCA in *E. coli* or in yeast versions of the same PCAs. Such screening can also be applied to enzymes whose targets are other proteins or nucleic acids for known enzyme/substrate pairs or to novel enzyme substrate pairs identified as described below.

Proteins involved in viral integration processes are examples of targets that could be tested for inhibitors using the PCA strategies. Examples for the HIV virus include:
i) inhibition of integrase or the transport of the pre-integration complex: protein Ma or vpr
ii) Inhibition of the cell cycle in G2 by vpr (interaction by cyclin B) causing induction of apoptosis.
iii) Inhibition of the interaction of gp160 (precursor of the membrane proteins) with furine.

Accessory proteins of HIV as a therapeutic target:
i) Vpr: nuclear localizing sequence (target): interaction site of vpr with phosphatasesA.
ii) vif: interaction with vimentin (cytoskeleton associated protein).
ii) Vpu: Degradation of CD4 in the RE mediated by the cytoplasmic tail of Vpu.
iii) nef: Myristoylation signal of Nef.

Other general targets for drug screening could include proteins linked neurodegenerative diseases, such as to alpha-synuclein. This protein has been linked to early onset of Parkinson disease and it is present also implicated in in Alzheimer disease. There is also β-amyloid proteins, linked to Alzheimers disease.

An example of protein-carbohydrate interactions that would be a target for drug screening includes the selectins that are generally implicated in inflammation. These cell surface glycoproteins are directly involved in diapedesis.

A number of tumor supressor genes whos actions are mediated by protein-protein interactions could be screened for potential anti-cancer compounds. These include PTEN, a tumor supressor directly involved in the formation of harmatomas. It is also involved in inherited breast and thyroid cancer. Other interesting tumor supressor genes include p53, Rb and BARC1.

EXAMPLE 6

Examples of Applications the PCA Strategy to Detect Enzyme/substrate Interactions The examples described above are used for identifying novel molecular interactions involving molecules that merely bind to each other. However detecting the substrates of enzymes is also fully compatible with the PCA strategy as shown below:
i) Enzymes that form tight complexes or with protein substrates or induce efficient PCA fragment assembly or
ii) Mutant enzymes that bind tightly to substrate but do not undergo product release because of mutations residues involved in nucleophilic attack and/or product release (substrate trapping).

Enzymes may form tight complexes with their substrates (Kd ~1–10 $\mu$M). In these cases PCA may be efficient enough to detect such interactions. However, even if this is not true, PCA may work to detect weaker interactions. Generally, if the rate of catalysis and product release is slower than the rate of folding-reassembly of the PCA complementary fragments, effectively irreversible folding and reconstitution of the PCA reporter activity will have occurred. Therefore, even if the enzyme and substrate are no longer interacting, the PCA signal is detected. Therefore, the detection of novel enzyme substrates using PCA may be possible, independent of effective substrate Kd or rate of product release. In cases where product release is much faster than PCA fragment assembly/folding and alternative approach is provided by generating substrate trapping" mutants of the test enzyme. An example of this approach applied to the protein tyrosine phosphatase PTP1B, where substrate trapping mutants have been generated by mutating the nucleophilic aspartate 181 to alanine rendering the enzyme cataliticly dead, but capable of forming tight complexes with a known substrate, the EGF receptor and other unknown proteins (Flint, A. J. et al. (1996) Proc. Natl. Acad. USA 941680–1685). An application of using PCA to screen for interacting partners of PTP1B is given as follows. We use the aminoglycoside kinase (AK)-based PCA in transiently transfected COS or 293 cells. The substrate trap mutant catalytic domain of PTP1B is fused to N-terminal complementary fragment of AK, while a C-terminal fusion of the other AK fragment is made to a cDNA library. Cells are co-transfected with complementary AK pairs and grown in selective concentrations of G418. After 72 hours, colonies of surviving cells are picked and in situ PCR is performed using primers designed to anneal to 3' and 5' flanking regions of the cDNA coding region. PCR amplified products are then 5' sequenced to identify the gene. Enzyme inhibitors Screening combinatorial libraries of compounds for those that inhibit enzyme-PROTEIN substrate complexes either with:
i) Enzymes that form tight complexes with protein substrates or
ii) Mutant enzymes that bind tightly to substrate but do not undergo product release because of the mutation.

EXAMPLE 7

Applications of the PCA Strategy to Protein Engineering/evolution

The PCA strategy can be used to generate peptides or proteins with novel binding properties that may have therapeutic value, as is done today with phage display technology. It is also possible to develop enzymes with novel substrate or physical properties for industrial enzyme development. Two detailed examples of the application of the PCA strategy to these ends are given below, with additional applications listed below.

1) Selection of high-affinity, heterodimerizing leucine zipper sequences (J. Pelletier, K. Arndt, A. Plueckthun and S. Michnick, manuscript in preparation). The mDHFR PCA, described above, was used in a scheme for the selection of efficiently heterodimerizing, designed leucine zippers. It has been proposed that the formation of salt bridges between positively and negatively charged residues at complementing "e" and "g" positions is important in stabilizing leucine zipper formation, though this view has been contested. In order to help define the importance of salt-bridge formation at the e and g positions, two leucine zipper libraries were built. Both are based on the GCN4 leucine zipper sequence, but contain sequence information specific to either Jun or Fos zippers in order to create heterodimerizing pairs. As well, the e-1 to e-4 and g-1 to g-4 positions in each library were randomized to code for positively or negatively charged residues, or neutral polar residues. These libraries were amplified by PCR and subcloned into the Z-F[1,2] or Z-F[3] constructs (described above) from which the GCN4 zipper sequences had been removed. The bacterial mDHFR PCA selection was performed on selective solid media, as described earlier. Colonies were picked and sequenced; sequence analysis reveals that the distribution of charged or neutral residues at e–g pairs is not random, but is biased toward pairing of opposite charges, or pairing of a charged with a neutral residue, rather than same-charge pairing (see FIG. 7). We reasoned that better zipper pairing should lead to an increase in efficiency of DHFR-fragment complementation, resulting in faster bacterial doubling times (see Table 1 in the mDHFR PCA description), and undertook a selection/enrichment of the novel zippers relative to GCN4, as follows. The designed zipper libraries, expressed as N-terminal fusions to the DHFR F[1,2] or F[3:I114A], were cotransformed, clones were picked, propagated and mixed in selective liquid culture, and the mix was added in a 1:1 000 000 ratio to clone Z-F[1,2]+Z-F[3:I114A] (original GCN4 leucine zippers). The mixture was propagated in selective liquid culture over multiple passages. Restriction analysis shows that within 4 passages, the population of GCN4-expressing bacteria is diminishing relative to the novel zipper sequences (data not shown), indicating that some of the designed zipper-containing clones are propagated at a higher rate than those containing GCN4. Bacteria from later passages were plated on selective medium, and individual clones sequenced to reveal the identity of the most successful designed zipper pairs (data not shown).

2) Application of PCA to enzyme function and design PCA Development Adenosine deaminase (ADA) meets all of the criteria for a PCA listed above. ADA is a small (~40 kD), and easily purified monomeric zinc metallo-enzyme and the structure of murine ADA has been resolved. Several in vitro ADA activity assays have been developed, involving UV spectrophotometry and stopped-flow fluorimetry. $E.\ coli$ ADA catalyzes the irreversible conversion of cytotoxic adenine nucleosides to non-toxic inosines.

Eukaryotic or prokaryotic cells propagated in the presence of cytotoxic concentrations of adenosine or adenosine analogs require ADA to detoxify these compounds. This is the basis of a dominant-selection strategy used to select for cells expressing a specific gene in mammalian cells. The ADA gene has also been expressed in SF3834 $E.\ coli$ cells which lack a gene coding for endogenous ADA. When the gene coding for ADA is introduced into ADA- bacterial DNA, those cells that express ADA are able to survive high concentrations of added adenosine; those that do not, die. This forms the basis of an in vivo ADA activity assay.

We chose ADA, principally because it can be used as a dominant selective marker in mammalian and bacterial cells where the gene has been knocked out. The reason we choose dominant selective genes is because in screening for novel protein-protein interactions, particularly testing for interactions of a known protein against a library of millions of independent clones, selection serves to filter for cells that may show a positive response for reasons having nothing to do with a specific protein-protein interaction. We will use three test systems of interacting proteins including leucine zipper-forming sequences, the proteins raf and p21 and the induced oligomerization system, FK506 binding protein (FKBP) and mTOR that interact through the macrocyclic immuno-suppressant compound rapamycin. For all of these systems, we will construct $E.\ coli$ and mammalian transient transfection plasmids and subclone the test proteins as fusions to ADA complementary fragments. The primary assay will be survival of SF3834 $E.\ coli$ cells that have been transformed with the complementary ADA fragments fused to the test oligomerization proteins in the presense of toxic concentrations of adenososine. We will then purify fusion proteins from colonies of and perform in vitro assays of ADA activity as described below. The utility of the ADA PCA as a method to identify novel proteins that interact with a test bait will be performed in mammalian COS-7 and HEK-293T cells transiently transfected with FKBP fused to one of the ADA fragments and the other fragment fused to a cDNA library from normal human spleen containing $10^6$ independent clones. As with the $E.\ coli$ assay, cells that survive in a medium containing toxic concentrations of ADA is collected and isolated plasmids will be testd to identify the gene for the interacting protein by PCR amplification and chain propagation-termination techniques.

Structural motifs required for protein function: Determination of the structural elements required for the enzymatic function of ADA are investigated through alteration of the structures of the enzyme fragments. At first, ADA is cut into two separate domains—one responsible for substrate binding (residues 1–210) and one responsible for catalysis (residues 211–352). These separate pieces will be attached to known assembly domains, such as leucine zippers (see example 1 above). Reassembly will restore activity which will be assessed through detailed in vitro kinetic analysis of the binding and catalytic properties of the re-assembled enzyme, using UV spectrophotometry and stopped-flow fluorimetry to observe the enzymatic reactions. This system will provide another handle on the manipulation of enzyme activity that will afford a powerful tool for enzymatic mechanism study. For example, the difference in the kinetic behaviour of the reassembled enzyme on mixing with the substrate, compared to enzyme reassembled in presence of substrate (where substrate may already be bound by binding domain) will allow sophisticated level of study of importance of binding energy to catalysis. Subsequent point mutations to the functional or assembly domains of the proteins will then allow a very subtle perturbation and detailed quantification of the relationship of binding energy to catalysis. This precise control over the structure and assembly of separate functional domains of the enzyme will permit very sophisticated enzymatic structure function studies, the definition of structural motifs and an understanding of their role in catalysis.

Novel protein catalyst design: The detailed knowledge of the enzyme mechanism gained through determination of the structural requirements for catalysis will then be exploited through the combination of these functional "building blocks" with the functional motifs responsible for substrate binding and catalysis in other enzymes, allowing the generation of novel protein catalysts. For example, the catalytic motif from ADA is modified to a cytidine-binding motif, creating a novel enzyme with potentially useful catalytic properties. The activity of these novel enzymes can easily be assessed through in vivo assays similar to that of the PCA system, or through in vitro activity assays. Furthermore, the detailed mechanistic investigation of the resulting enzymes possible with this system will permit the rational design of each subsequent generation of catalysts.

EXAMPLE 8

Examples of Applications the PCA Strategy to Detect Molecular Interactions in Whole Organisms It is a logical extension of the descriptions of PCA applications above to the utility of these techniques in whole model organisms such as drosophila, nematodes, zebra fish and puffer fish, as examples. The sole differences with other listed examples is that vectors used would need to be different (for example retroviral vectors) and that any substrates needed by the PCA would need to be bioavailable, or detection would need to be performed in situ.

EXAMPLE 9

Examples of Applications of the PCA Strategy to Gene Therapy

Another important embodiment of the invention is to provide a means and method for gene therapy of mammalian disease. Of particular interest is the use of PCA therapeutic for treatment of cancer. In one embodiment of said PCA gene therapy, a PCA is developed employing fragments (modular protein units) derived from a protein toxin for example: Pseudomonas exotoxin, Diptheria toxin and the plant toxin gelonin, or other like molecules. For therapy of breast cancer for example, first a mammalian, retroviral, adenoviral, or eukaryotic artificial chromosomal (EAC's) genetic construct is prepared that introduces one fragment of the selected toxin under the control of the promoter for expression of the erbB2 oncogene. Its is well known that the erbB2 oncogene is overexpressed in breast cancer and adenocarcinoma cells (D. J. Slamon et. al., Science, 1989, 244, 707). The HER21neu (c-erbB-2) proto-oncogene encodes a sub-class 1 185-kDa transmembrane protein tyrosine kinase growth factor receptor, $p185^{HER2}$. Also, the human erbB2 oncogene is located on chromosome 17, region q21 and comprises 4,480 base pairs and $p185^{HER2}$ serves as a receptor for a 30-kDa glycoprotein growth factor secreted by human breast cancer cell lines (R. Lupu et. Al., Science, 1990, 249, 1152).

The transgene is introduced 'in vivo' or 'ex-vivo' into target cells employing methods known by those skilled in the art e.g. homologous recombination to insert transgene into locus of interest via retroviral, adenoviral or EAC's. A second genetic construct comprising a fusion gene containing a target DNA that encodes an interacting protein that interacts with erbB2 oncogene discovered by the PCA process described in this invention and the "second" fragment of the toxin molecule. This construct is delivered to the patient by methods known in the art for example as shown in U.S. Pat. Nos. 5,399,346 and 5,585,237 whose entire contents are incorporated by reference herein. Transgene expression of the erbB2 oncogene-toxin fragment described will now be under the control of the constitutive oncogene promoter. Proliferating tumor cells will thus produce one piece of the toxin attached as a fusion to the erbB2 oncogene. In the presence of the second genetic construct expressing the PCA discovered interacting erbB2 oncogene "interacting protein—toxin fragment" construct then: erbB2 oncogene-toxin fragmentA: interacting protein-toxin fragment B will be created and induce death of target tumor cells through creation of an active toxin through Protein Fragment Complementation and thus provide an efficacious and efficient therapy of said disease.

This can be extended to other diseases and other toxins employing techniques described and embodied in this invention.

EXAMPLE 10

Examples of Applications the PCA Strategy to Detect Molecular Interactions in Vitro Any of the PCA strategies described above could be addapted to in vitro detection. Unlike the in vivo PCAs however, detection would be performed with purified PCA fragment-fusion proteins. Such uses of PCA have the potential for use in diagnostic kits. For example the test DHFR assay described above where the interactiing domains are FKBP12 and TOR could be used as a diagnostic test for rapamycin concentrations for use in monitoring dossage in patients treated with this drug.

As shown above, the instant invention provides:
1) Allow for the detection of protein-protein interactions in vivo or in vitro.
2) Allow for the detection of protein-protein interactions in appropriate contexts, such as within a specific organism, cell type, cellular compartment, or organelle.
3) Allow for the detection of induced versus constitutive protein-protein interactions (such as by a cell growth or inhibitory factor).
4) To be able to distinguish specific-versus non-specific protein-protein interactions by controlling the sensitivity of the assay.
5) Allow for the detection of the kinetics of protein assembly in cells.
6) Allow for screening of cDNA libraries for protein-protein interactions.

Further aspects of the invention can be demonstrated by identifying novel interactions with the enzyme p70S6k, to determine its regulation and how separate signaling cascades converge on this enzyme.

The PCA method is particularly useful for detection of the kinetics of protein assembly in cells. The kinetics of protein assembly can be determined using fluorescent protein systems.

In a further embodiment of the invention, PCA can be used for drug screening. The techniques of PCA are used to screen for drugs that block specific biochemical pathways in cells allowing for a carefully targeted and controlled method for identifying products that have useful pharmacological properties.

Although the present invention has been described herein above by way of preferred embodiments thereof, it can be modified, without departing from the spirit and nature of the subject invention as defined in the appended claims.

REFERENCES

1. Reed, L. J.:Multienzyme Complexes. Acc. Chem. Res. 7,40–46 (1974).

2. Lander, E. S.:The new genomics—global views of biology. Science 274, 536–539 (1996).
3. Evangelista, C., Lockshon, D. & Fields, S.:The yeast two-hybrid system—prospects for protein linkage maps. Trends in Cell Biology 6, 196–199 (1996).
4. Guarente, L.:Strategies for the identification of interacting proteins. [Review]. Proc. Natl. Acad. Sci. USA 90,1639–41 (1993).
5. Adams, S. R., Harootunian, A. T., Buechler, Y. J., Taylor, S. S. & Tsien, R. Y.:Fluorescence ratio imaging of cyclic AMP in single cells. Nature 349, 694–7 (1991).
6. Chien, C. T., Bartel, P. L., Sternglanz, R. & Fields, S.:The two-hybrid system: a method to identify and clone genes for proteins that interact with a protein of interest. Proc. Natl. Acad. Sci. USA 88, 9578–82 (1991).
7. Fields, S. & Song, O.:A novel genetic system to detect protein-protein interactions. Nature 340, 245–6 (1989).
8. Gyuris, J., Golemis, E., Chertkov, H. & Brent, R.:Cdil, a human G1 and S phase protein phosphatase that associates with Cdk2. Cell 75, 791–803 (1993).
9. Johnsson, N. & Varshavsky, A.:Split ubiquitin as a sensor of protein interactions in vivo. Proc. Natl. Acad. Sci. USA 91, 10340–4 (1994).
10. Volz, K. W., Matthews, D. A., Alden, R. A., Freer, S. T., Hansch, C., Kaufman, B. T. & Kraut, J.:Crystal structure of avian dihydrofolate reductase containing phenyltriazine and NADPH. J. Biol. Chem. 257, 2528–36 (1982).
11. Oefner, C., D'Arcy, A. & Winkler, F. K.:Crystal structure of human dihydrofolate reductase complexed with folate. Eur. J. Biochem. 174, 377–85 (1988).
12. Filman, D. J., Bolin, J. T., Matthews, D. A. & Kraut, J.:Crystal structures of *Escherichia coli* and Lactobacillus casei dihydrofolate reductase refined at 1.7 A resolution. II. Environment of bound NADPH and implications for catalysis. J. Biol. Chem. 257,13663–72 (1982).
13. Bystroff, C. & Kraut, J.:Crystal structure of unliganded *Escherichia coli* dihydrofolate reductase. Ligand-induced conformational changes and cooperativity in binding. Biochemistry 30, 2227–39 (1991).
14. Appleman, J. R., Prendergast, N., Delcamp, T. J., Freisheim, J. H. & Blakley, R. L.:Kinetics of the formation and isomerization of methotrexate complexes of recombinant human dihydrofolate reductase. J. Biol. Chem. 263, 10304–13 (1988).
15. Loetscher, P., Pratt, G. & Rechsteiner, M.:The C terminus of mouse ornithine decarboxylase confers rapid degradation on dihydrofolate reductase. Support for the pest hypothesis. J. Biol. Chem. 266, 11213–20 (1991).
16. Kaufman, R. J., Davies, M. V., Pathak, V. K. & Hershey, J. W.:The phosphorylation state of eucaryotic initiation factor 2 alters translational efficiency of specific mRNAs. Mol. Cell. Biol. 9, 946–58 (1989).
17. Stammers, D. K., Champness, J. N., Beddell, C. R., Dann, J. G., Eliopoulos, E., Geddes, A. J., Ogg, D. & North, A. C.:The structure of mouse L1210 dihydrofolate reductase-drug complexes and the construction of a model of human enzyme. FEBS Left. 218, 178–84 (1987).
18. Gegg, C. V., Bowers, K. E. & Matthews, C. R. in Techniques in Protein Chemistry (eds. Marshak, D. R.) 439–448 (Academic Press, New York, USA, 1996).
19. Perry, K. M., Onuffer, J. J., Gittelman, M. S., Barmat, L. & Matthews, C. R.:Long-range electrostatic interactions can influence the folding, stability, and cooperativity of dihydrofolate reductase. Biochemistry 28, 7961–8 (1989).
20. Bullerjahn, A. M. & Freisheim, J. H.:Site-directed deletion mutants of a carboxyl-terminal region of human dihydrofolate reductase. J. Biol. Chem. 267, 864–70 (1992).
21. Buchwalder, A., Szadkowski, H. & Kirschner, K.:A fully active variant of dihydrofolate reductase with a circularly permuted sequence. Biochemistry 31, 1621–30 (1992).
22. Chen, X., Rambo, R. & Matthews, C. R.:Amino acid replacements can selectively affect the interaction energy of autonomous folding units in the alpha subunit of tryptophan synthase. Biochemistry 31, 2219–23 (1992).
23. Prevost, M., Wodak, S. J., Tidor, B. & Karplus, M.:Contribution of the hydrophobic effect to protein stability: analysis based on simulations of the Ile-96-Ala mutation in barnase. Proc. Natl. Acad. Sci. USA 88,10880–4 (1991). 24. Kellis, J., Jr., Nyberg, K., Sali, D. & Fersht, A. R.:Contribution of hydrophobic interactions to protein stability. Nature 333, 784–6 (1988).
25. Kellis, J., Jr., Nyberg, K. & Fersht, A. R.:Energetics of complementary side-chain packing in a protein hydrophobic core. Biochemistry 28, 4914–22 (1989).
26. Henderson, G. B., Russell, A. & Whiteley, J. M.:A fluorescent derivative of methotrexate as an intracellular marker for dihydrofolate reductase in L 1210 cells. Arch. Biochem. Biophys. 202, 29–34 (1980).
27. Denzer, A. J., Nabholz, C. E. & Spiess, M.:Transmembrane orientation of signal-anchor proteins is affected by the folding state but not the size of the N-terminal domain. EMBO J. 14, 6311–7 (1995).
28. Spiess, M., Schwartz, A. L. & Lodish, H. F.:Sequence of human asialoglycoprotein receptor cDNA. An internal signal sequence for membrane insertion. J. Biol. Chem. 260,1979–82 (1985).
29. Picard, V., Ersdal-Badju, E., Lu, A. & Bock, S. C.:A rapid and efficient one-tube PCR-based mutagenesis technique using Pfu DNA polymerase. Nucleic Acids Res. 22, 2587–91 (1994).
30. Kunkel, T. A., Roberts, J. D. & Zakour, R. A.:Rapid and efficient site-specific mutagenesis without phenotypic selection. Methods Enzymol. 154, 367–82 (1987).
31. Tartof, K. D. & Hobbs, C. A.:New cloning vectors and techniques for easy and rapid restriction mapping. Gene 67,169–82 (1988).
32. Laemmli, U. K.:Cleavage of structural proteins during the assembly of the head of bacteriophage T4. Nature 227, 680–5 (1970).
33. Ellenberger, T. E., Brandl, C. J., Struhl, K. & Harrison, S. C.:The GCN4 basic region leucine zipper binds DNA as a dimer of uninterrupted alpha helices: crystal structure of the protein-DNA complex. Cell 71,1223–37 (1992).
34. Cody, V., Luft, J. R., Ciszak, E., Kalman, T. I. & Freisheim, J. H.:Crystal structure determination at 2.3 A of recombinant human dihydrofolate reductase ternary complex with NADPH and methotrexate-gamma-tetrazole. Anti Cancer Drug Des. 7, 483–91 (1992).
101. Reed, L. J.:Multienzyme Complexes. Acc. Chem. Res. 7, 40–46 (1974).
102. Guarente, L.:Strategies for the identification of interacting proteins. Proc. Natl. Acad. Sci. USA 90,1639–41 (1993).
103. Adams, S. R., Harootunian, A. T., Buechler, Y. J., Taylor, S. S. & Tsien, R. Y.:Fluorescence ratio imaging of cyclic AMP in single cells. Nature 349, 694–7 (1991).
104. Chien, C. T., Bartel, P. L., Sternglanz, R. & Fields, S.:The two-hybrid system: a method to identify and clone genes for proteins that interact with a protein of interest. Proc. Natl. Acad. Sci. USA 88, 9578–82 (1991).
105. Fields, S. & Song, O.:A novel genetic system to detect protein-protein interactions. Nature 340, 245–6 (1989).
106. Gyuris, J., Golemis, E., Chertkov, H. & Brent, R.:Cdil, a human G1 and S phase protein phosphatase that associates with Cdk2. Cell 75, 791–803 (1993).

107. Guarente, L.:Strategies for the identification of interacting proteins. Proc. Natl. Acad. Sci. USA 90,1639–41 (1993).

108. Johnsson, N. & Varshavsky, A.:Split ubiquitin as a sensor of protein interactions in vivo. Proc. Natl. Acad. Sci. USA 91,10340–4 (1994). 109. O'Shea, E. K., Klemm, J. D., Kim, P. S. & Alber, T.:X-ray structure of the GCN4 leucine zipper, a two-stranded, parallel coiled coil. Science 254, 539–44 (1991).

110. Ellenberger, T. E., Brandl, C. J., Struhl, K. & Harrison, S. C.:The GCN4 basic region leucine zipper binds DNA as a dimer of uninterrupted alpha helices: crystal structure of the protein-DNA complex. Cell 71,1223–37 (1992).

111. Volz, K. W., Matthews, D. A., Alden, R. A., Freer, S. T., Hansch, C., Kaufman, B. T. & Kraut, J.:Crystal structure of avian dihydrofolate reductase containing phenyltriazine and NADPH. J. Biol. Chem. 257, 2528–36 (1982).

112. Oefner, C., D'Arcy, A. & Winkler, F. K.:Crystal structure of human dihydrofolate reductase complexed with folate. Eur. J. Biochem. 174, 377–85 (1988).

113. Filman, D. J., Bolin, J. T., Matthews, D. A. & Kraut, J.:Crystal structures of *Escherichia coli* and *Lactobacillus casei* dihydrofolate reductase refined at 1.7 A resolution. II. Environment of bound NADPH and implications for catalysis. J. Biol. Chem. 257,13663–72 (1982).

114. Bystroff, C. & Kraut, J.:Crystal structure of unliganded *Escherichia coli* dihydrofolate reductase. Ligand-induced conformational changes and cooperativity in binding. Biochemistry 30, 2227–39 (1991).

115. Jones, B. E. & Matthews, C. R.:Early intermediates in the folding of dihydrofolate reductase from *Escherichia coli* detected by hydrogen exchange and NMR. Protein Sci. 4, 167–77 (1995).

116. Jennings, P. A., Finn, B. E., Jones, B. E. & Matthews, C. R.:A reexamination of the folding mechanism of dihydrofolate reductase from *Escherichia coli*: verification and refinement of a four-channel model. Biochemistry 32, 3783–9 (1993).

117. Fierke, C. A., Johnson, K. A. & Benkovic, S. J.:Construction and evaluation of the kinetic scheme associated with dihydrofolate reductase from *Escherichia coli*. Biochemistry 26, 4085–92 (1987).

118. Andrews, J., Fierke, C. A., Birdsall, B., Ostler, G., Feeney, J., Roberts, G. C. & Benkovic, S. J.:A kinetic study of wild-type and mutant dihydrofolate reductases from Lactobacillus casei. Biochemistry 28, 5743–50 (1989).

10 119. Thillet, J., Adams, J. A. & Benkovic, S. J.:The kinetic mechanism of wild-type and mutant mouse dihydrofolate reductases. Biochemistry 29, 5195–202 (1990).

120. Hillcoat, B. L., Nixon, P. F. & Blakley, R. L.:Effect of substrate decomposition on the spectrophotometric assay of dihydrofolate reductase. Anal. Biochem. 21, 178–89 (1967).

121. Appleman, J. R., Prendergast, N., Delcamp, T. J., Freisheim, J. H. & Blakley, R. L.:Kinetics of the formation and isomerization of methotrexate complexes of recombinant human dihydrofolate reductase. J. Biol. Chem. 263, 10304–13 (1988).

122. Grange, T., Kunst, F., Thillet, J., Ribadeau-Dumas, B., Mousseron, S., Hung, A., Jami, J. & Pictet, R.:Expression of the mouse dihydrofolate reductase cDNA in B. subtilis: a system to select mutant cDNAs coding for methotrexate resistant enzymes. Nucleic Acids Res. 12, 3585–601 (1984).

123. Loetscher, P., Pratt, G. & Rechsteiner, M.:The C terminus of mouse ornithine decarboxylase confers rapid degradation on dihydrofolate reductase. Support for the pest hypothesis. J. Biol. Chem. 266,11213–20 (1991).

124. Hao, H., Tyshenko, M. G. & Walker, V. K.:Dihydrofolate reductase of Drosophila. Cloning and expression of a gene with a rare transcript. J. Biol. Chem. 269, 15179–85 (1994).

125. Kaufman, R. J.:Identification of the components necessary for adenovirus translational control and their utilization in cDNA expression vectors. Proc. Natl. Acad. Sci. USA 82, 689–93 (1985).

126. Kaufman, R. J., Davies, M. V., Pathak, V. K. & Hershey, J. W.:The phosphorylation state of eucaryotic initiation factor 2 alters translational efficiency of specific mRNAs. Mol. Cell. Biol. 9, 946–58 (1989).

127. Oefner, C., D'Arcy, A. & Winkler, F. K.:Crystal structure of human dihydrofolate reductase complexed with folate. Eur. J. Biochem. 174, 377–85 (1988).

128. Stammers, D. K., Champness, J. N., Beddell, C. R., Dann, J. G., Eliopoulos, E., Geddes, A. J., Ogg, D. & North, A. C.:The structure of mouse L1210 dihydrofolate reductase-drug complexes and the construction of a model of human enzyme. FEBS Lett. 218,178–84 (1987).

129. Gegg, C. V., Bowers, K. E. & Matthews, C. R. in Techniques in Protein Chemistry (eds. Marshak, D. R.) 439–448 (Academic Press, New York, USA, 1996).

130. Bystroff, C. & Kraut, J.:Crystal structure of unliganded *Escherichia coli* dihydrofolate reductase. Ligand-induced conformational changes and cooperativity in binding. Biochemistry 30, 2227–39 (1991).

131. Harmann, B. & Kilimann, M. W.:cDNA encoding a 59 kDa homolog of ribosomal protein S6 kinase from rabbit liver. FEBS Lett. 273, 248–52 (1990).

132. Kozma, S. C., Ferrari, S., Bassand, P., Siegmann, M., Totty, N. & Thomas, G.:Cloning of the mitogeN-activated S6 kinase from rat liver reveals an enzyme of the second messenger subfamily. Proc. Natl. Acad. Sci. USA 87, 7365–9 (1990).

133. Grove, J. R., Banerjee, P., Balasubramanyam, A., Coffer, P. J., Price, D. J., Avruch, J. & Woodgett, J. R.:Cloning and expression of two human p70 S6 kinase polypeptides differing only at their amino termini. Mol. Cell. Biol. 1 1, 5541–50 (1991).

134. Banerjee, P., Ahmad, M. F., Grove, J. R., Kozlosky, C., Price, D. J. & Avruch, J.:Molecular structure of a major insulin/mitogeN-activated 70-kDa S6 protein kinase. Proc. Natl. Acad. Sci. USA 87, 8550–4 (1990).

135. Reinhard, C., Thomas, G. & Kozma, S. C.:A single gene encodes two isoforms of the p70 S6 kinase: activation upon mitogenic stimulation. Proc. Natl. Acad. Sci. USA 89, 4052–6 (1992).

136. Reinhard, C., Fernandez, A., Lamb, N. J. & Thomas, G.:Nuclear localization of p85S6k: functional requirement for entry into S phase. EMBO J. 13,1557–65 (1994).

137. Chung, J., Kuo, C. J., Crabtree, G. R. & Blenis, J.:RapamyciN-FKBP specifically blocks growth-dependent activation of and signaling by the 70 kd S6 protein kinases. Cell 69,1227–36 (1992). 138. Price, D. J., Grove, J. R., Calvo, V., Avruch, J. & Bierer, B. E.:RapamyciN-induced inhibition of the 70-kilodalton S6 protein kinase. Science 257, 973–7 (1992).

139. Kuo, C. J., Chung, J., Fiorentino, D. F., Flanagan, W. M., Blenis, J. & Crabtree, G. R.:Rapamycin selectively inhibits interleukiN-2 activation of p70 S6 kinase. Nature 358, 70–3 (1992).

140. Terada, N., Franklin, R. A., Lucas, J. J., Blenis, J. & Gelfand, E. W.:Failure of rapamycin to block proliferation once resting cells have entered the cell cycle despite 141. Calvo, V., Crews, C. M., Vik, T. A. & Bierer, B. E.:lnterleukin 2 stimulation of p70 S6 kinase activity is inhibited by the immunosuppressant rapamycin. Proc. Natl. Acad. Sci. USA 89, 7571–5 (1992).
142. Weng, Q. P., Andrabi, K., Kozlowski, M. T., Grove, J. R. & Avruch, J.:Multiple independent inputs are required for activation of the p70 S6 kinase. Mol. Cell. Biol. 15, 2333–40 (1995).
143. Ming, X. F., Burgering, B. M., Wennstrom, S., ClaessoN-Weish, L., Heldin, C. H., Bos, J. L., Kozma, S. C. & Thomas, G.:Activation of p70/p85 S6 kinase by a pathway independent of p21 ras [see comments]. Nature 371, 426–9 (1994).
144. Cheatham, L., Monfar, M., Chou, M. M. & Blenis, J.:Structural and functional analysis of pp70S6k. Proc. Natl. Acad. Sci. USA 92,11696–700 (1995).
145. Flotow, H. & Thomas, G.:Substrate recognition determinants of the mitogeN-activated 70K S6 kinase from rat liver. J. Biol. Chem. 267, 3074–8 (1992).
146. Wendt, H., Baici, A. & Bosshard, H. R.:Mechanism of assembly of a leucine zipper domain. J. Am. Chem. Soc. 116, 6973–6974 (1994).
147. Mahalingam, M. & Templeton, D. J.:Constitutive activation of S6 kinase by deletion of amino-terminal autoinhibitory and rapamycin sensitivity domains. Mol. Cell. Biol. 16, 405–13 (1996).
148. Edery, I., Chu, L. L., Sonenberg, N. & Pelletier, J.:An efficient strategy to isolate full-length cDNAs based on an mRNA cap retention procedure (CAPture). Mol. Cell. Biol. 15, 3363–71 (1995).
149. Hussain, A., Lewis, D., Yu, M. & Melera, P. W.:Construction of a dominant selectable marker using a novel dihydrofolate reductase. Gene 112,179–88 (1992).
150. Lim, K., Ho, J. X., Keeling, K., Gilliland, G. L., Ji, X., Ruker, F. & Carter, D. C.:Three-dimensional structure of Schistosoma japonicum glutathione S-transferase fused with a six-amino acid conserved neutralizing epitope of gp4l from HIV. Protein Sci. 3, 2233–44 (1994).
151. Habig, W. H., Keen, J. H. & Jakoby, W. B.:Glutathione S-transferase in the formation of cyanide from organic thiocyantes and as an organic nitrate reductase. Biochemical & Biophysical Research Communications 64, 501–6 (1975).
152. Chalfie, M., Tu, Y., Euskirchen, G., Ward, W. W. & Prasher, D. C.:Green fluorescent protein as a marker for gene expression. Science 263, 802–5 (1994).
153. Cody, C. W., Prasher, D. C., Westler, W. M., Prendergast, F. G. & Ward, W. W.:Chemical structure of the hexapeptide chromophore of the Aequorea greeN-fluorescent protein. Biochemistry 32,1212–8 (1993).
154. Morin, J. G. & Hastings, J. W.:Energy transfer in a bioluminescent system. Journal of Cellular Physiology 77, 313–8 (1971).
155. Morise, H., Shimomura, O., Johnson, F. H. & Winant, J.:lntermolecular energy transfer in the bioluminescent system of Aequorea. Biochemistry 13, 2656–62 (1974).
156. Ward, W. W. & Bokman, S. H.:Reversible denaturation of Aequorea greeN-fluorescent protein: physical separation and characterization of the renatured protein. Biochemistry 21, 4535–40 (1982).
25 157. Heim, R., Prasher, D. C. & Tsien, R. Y.:Wavelength mutations and posttranslational autoxidation of green fluorescent protein. Proc. Natl. Acad. Sci. USA 91, 12501–4 (1994).
158. Ormo, M., Cubitt, A. B., Kallio, K., Gross, L. A., Tsien, R. Y. & Remington, S. J.:Crystal structure of the aequorea victoria green fluorescent protein. Science 273, 1392–1395 (1996).
159. Youvan, D. C. & Michelbeyerle, M. E.:Structure and fluorescence mechanism of gfp. Nature Biotechnology 14,1219–1220 (1996).
160. DeLuca, M., Woods,K.:Photographic Detection of luminescence in *Escherichia coli* Contaning the Gene for Firefly luciferase. Analytical Biochemestry 161, 501–507 (1986).
161. Conti, E., Franks, N. P., Brick, P.:Crystal structure of firefly luciferase throws light on a superfamily of adenylate -forming enymes. Structure 4, 287–298 (1996).
162. Magrath, I. T., Gupta, A., Jain, V. K.:A Rapid Screening Method for Bacteria Contaning Firefly Luciferase Plasmids. Biotechniques 15, 4–6 (1993).

Abbreviations: PCA, Protein-fragment Complementation Assay; mDHFR, murine dihydrofolate reductase; hDHFR, human dihydrofolate reductase; Z-F[1,2], GCN4 leucine zipper-mDHFR fragment[1,2]; USPS, ubiquitiN-based split-protein sensor; IPTG, isopropyl-b-D-thiogalactopyranoside; PMSF, phenylmethylsulfonyl fluoride; SDS-PAGE, SDS polyacrylamide gel electrophoresis.

What is claimed is:

1. Protein fragment complementation assays for the detection of molecular interactions comprising a reassembly of separate fragments of a monomeric enzyme wherein reassembly of the monomeric enzyme fragments is operated by the interaction of molecular domains fused to each monomeric enzyme fragment, wherein reassembly of the monomeric enzyme fragments is independent of other molecular processes and wherein said reassembly is detected by means of reconstitution of activity of said enzyme.

2. A method for detecting biomolecular interactions said method comprising:
   (a) selecting an appropriate monomeric enzyme reporter molecule;
   (b) effecting fragmentation of said monomeric enzyme reporter molecule such that said fragmentation results in reversible loss of reporter function;
   (c) fusing or attaching fragments of said monomeric enzyme reporter molecule separately to other molecules;
   (d) reassociating said monomeric enzyme reporter fragments through interactions of the molecules that are fused or attached to said fragments; and
   (e) detecting the activity of said enzyme reporter molecule.

3. A method of testing biomolecular interactions comprising:
   a) generating a first fusion product comprising:
      i) a first fragment of a first monomeric enzyme molecule and
      ii) a second molecule which is different from said first molecule;
   b) generating a second fusion product comprising
      i) a second monomeric enzyme fragment of said first molecule; and
      ii) a third molecule which is different from said first molecule or second molecule;
   c) allowing the first and second fusion products to contact each other; and
   d) testing for activity regained by association of the enzyme fragments of the first molecule, wherein said reassociation is mediated by interaction of the second and third molecules.

4. A method comprising an assay where fragments of a first monomeric enzyme molecule are fused to a second molecule and fragment association is detected by reconstitution of the first enzyme molecule's activity.

5. A composition comprising a product selected from the group consisting of:
   (a) a first fusion product comprising:
      1) a first fragment of a first monomeric enzyme molecule whose fragments exhibit a detectable activity when associated and
      2) a second molecule that is fused to said first fragment;
   (b) a second fusion product comprising
      1) a second fragment of said first monomeric enzyme molecule and
      2) a third molecule that is fused to said second fragment; and
   c) both (a) and (b).

6. A composition comprising complementary fragments of a first monomeric enzyme molecule that exhibits a detectable activity when associated, wherein each fragment is fused to a separate molecule.

7. A composition comprising a nucleic acid molecule coding for a enzyme fusion product, which molecule comprises sequences coding for a product selected from the group consisting of:
   (a) a first enzyme fusion product comprising:
      1) fragments of a first monomeric enzyme molecule whose fragments can exhibit a detectable activity when associated and
      2) a second molecule fused to the fragment of the first molecule;
   (b) a second fusion product comprising
      1) a second fragment of said first monomeric enzyme molecule and
      2) a second or third molecule; and
   (c) both (a) and (b).

8. A method of testing for biomolecular interactions associated with: (a) complementary fragments of a first monomeric enzyme molecule whose fragments can exhibit a detectable activity when associated, said method comprising:
   1) creating a fusion of
      (a) a first fragment of a first monomeric enzyme molecule whose fragments can exhibit a detectable activity when associated and
      (b) a first protein-protein interacting domain;
   2) creating a fusion of
      (a) a second fragment of said first monomeric enzyme molecule and (b) a second or third protein-protein interacting domain that can bind said first protein-protein interacting domain;
   3) allowing the fusions of (1) and (2) to contact each other; and
   4) testing for reconstitution of said enzyme activity.

9. A composition comprising a product selected from the group consisting of:
   (a) a first fusion product comprising:
      1) a first fragment of a monomeric enzyme molecule whose fragments exhibit a detectable activity when associated and
      2) a first protein-protein interacting domain;
   (b) a second fusion product comprising
      1) a second fragment of said first monomeric enzyme molecule and
      2) a second protein-protein interacting domain that can bind said first protein-protein interacting domain; and
   (c) both (a) and (b).

10. A composition comprising a nucleic acid molecule coding for an enzyme fusion product, which molecule comprises sequences coding for either:
    (a) a first fusion product comprising:
       1) a first fragment of a monomeric enzyme molecule whose fragments exhibit a detectable activity when associated and
       2) a first protein-protein interacting domain; or
    (b) a second fusion product comprising
       1) a second fragment of said monomeric enzyme molecule and
       2) a second protein-protein interacting domain that can bind said first protein-protein interacting domain; or
    (c) both (a) and (b).

11. A method of screening a cDNA library comprising performing an enzyme complementation assay wherein said assay detection means is reconstitution of enzyme activity said enzyme being monomeric.

12. A method for detecting biomolecular interactions said method comprising:
    (a) selecting an appropriate monomeric enzyme reporter molecule;
    (b) effecting fragmentation of said monomeric enzyme reporter molecule;
    (c) fusing or attaching fragments of said monomeric enzyme reporter molecule separately to other molecules; followed by
    (d) reassociation of said reporter fragments through interactions of the molecules that are fused to said fragments; and
    (e) detecting said biomolecular interactions by reconstitution of enzyme activity.

13. A method for detecting biomolecular interactions said method comprising:
    (a) selecting an appropriate reporter molecule selected from the group consisting of a monomeric enzyme, a fluorescent protein, a luminescent protein and a phosphorescent protein;
    (b) effecting fragmentation of said reporter molecule such that said fragmentation results in reversible loss of reporter function;
    (c) fusing or attaching fragments of said reporter molecule separately to other molecules; followed by
    (d) reassociation of said reporter fragments through interactions of the molecules that are fused to said fragments; and
    (e) detecting said biomolecular interactions by reconstitution of activity of the reporter molecule.

14. Protein fragment complementation assays for the detection of molecular interactions comprising a reassembly of separate fragments of an enzyme having a molecular weight in the range of 10–40 KDa wherein reassembly of the enzyme fragments is operated by the interaction of molecular domains fused to each enzyme fragment, wherein reassembly of the enzyme fragments is independent of other molecular processes and wherein said reassembly is detected by means of reconstitution of activity of said enzyme.

15. The assay of claim 1 which comprises using a composition comprising complementary fragments of a first monomeric enzyme molecule, each fused to a separate molecule.

16. An assay according to claim 1 which comprises using a composition comprising a product selected from the group consisting of:

(a) a first fusion product comprising:
  1) a first fragment of a monomeric enzyme molecule whose fragments can exhibit a detectable activity when associated and
  2) a first protein-protein interacting domain;
(b) a second fusion product comprising
  1) a second fragment of said first monomeric enzyme molecule and
  2) a second protein-protein interacting domain that can bind said first protein-protein interacting domain; and (c) both (a) and (b).

17. A method of detecting kinetics of protein assembly comprising the method of any one of claims 1, 2, 3, 4 or 8 wherein time dependent reconstitution of enzyme activity is the detecting means.

18. A method according to any one of claims 1, 2, 3, 4, 8, or 11 wherein a chromogenic, fluorogenic, enzymatic, cell survival assay or other detectable signal is generated.

* * * * *